United States Patent
Maldiney et al.

(10) Patent No.: US 9,877,653 B2
(45) Date of Patent: Jan. 30, 2018

(54) PERSISTENT LUMINESCENCE NANOPARTICLES EXCITABLE IN SITU FOR IN VIVO OPTICAL IMAGING, IN VIVO MULTIMODAL OPTICAL—MRI IMAGING, AND THERANOSTICS

(71) Applicant: Centre National de la Recherche Scientifique (CNRS), Paris (FR)

(72) Inventors: Thomas Maldiney, Paris (FR); Cyrille Richard, Montigny le Bretonneux (FR); Daniel Scherman, Paris (FR); Didier Gourier, Paris (FR); Bruno Viana, Montgeron (FR); Aurelie Bessiere, Paris (FR)

(73) Assignee: Centre National de la Recherche Scientifique (CNRS) (FR)

( * ) Notice: Subject to any disclaimer, the term of this patent is extended or adjusted under 35 U.S.C. 154(b) by 455 days.

(21) Appl. No.: 14/375,234

(22) PCT Filed: Jan. 30, 2013

(86) PCT No.: PCT/EP2013/051727
§ 371 (c)(1),
(2) Date: Jul. 29, 2014

(87) PCT Pub. No.: WO2013/113721
PCT Pub. Date: Aug. 8, 2013

(65) Prior Publication Data
US 2014/0371575 A1    Dec. 18, 2014

(30) Foreign Application Priority Data

Jan. 30, 2012   (FR) .................................. 12 50846

(51) Int. Cl.
*A61B 5/00* (2006.01)
*A61K 49/00* (2006.01)
(Continued)

(52) U.S. Cl.
CPC ............ *A61B 5/0071* (2013.01); *A61B 5/055* (2013.01); *A61B 90/39* (2016.02);
(Continued)

(58) Field of Classification Search
CPC ....... A61B 5/0071; A61B 90/39; A61B 5/055; A61K 49/0093; A61K 49/186; C01G 15/00; C01G 15/006
See application file for complete search history.

(56) References Cited

U.S. PATENT DOCUMENTS

| | | | |
|---|---|---|---|
| 8,709,383 B2* | 4/2014 | Scherman | A61K 49/0067 424/9.1 |
| 8,932,486 B2* | 1/2015 | Jia | C09K 11/7774 252/301.4 F |
| 2013/0023714 A1* | 1/2013 | Johnston | A61K 9/0009 600/1 |

FOREIGN PATENT DOCUMENTS

| | | |
|---|---|---|
| FR | 2908891 A1 | 5/2008 |
| WO | 2007048856 A1 | 5/2007 |

OTHER PUBLICATIONS

Bessière et al. ZnGa2O4:Cr3+: a new red long-lasting phosphor with high brightness. Opt Express. May 23, 2011;19(11):10131-7.*
(Continued)

*Primary Examiner* — Jennifer Dieterle
*Assistant Examiner* — Helene Bor
(74) *Attorney, Agent, or Firm* — Banner & Witcoff, Ltd.

(57) ABSTRACT

Multimodal optical and magnetic resonance imaging methods based on the use of persistent luminescence nanoparticles. Use of mesoporous persistent luminescence <<core-shell>> complexes for theranostic applications.

19 Claims, 15 Drawing Sheets

Figure 1:
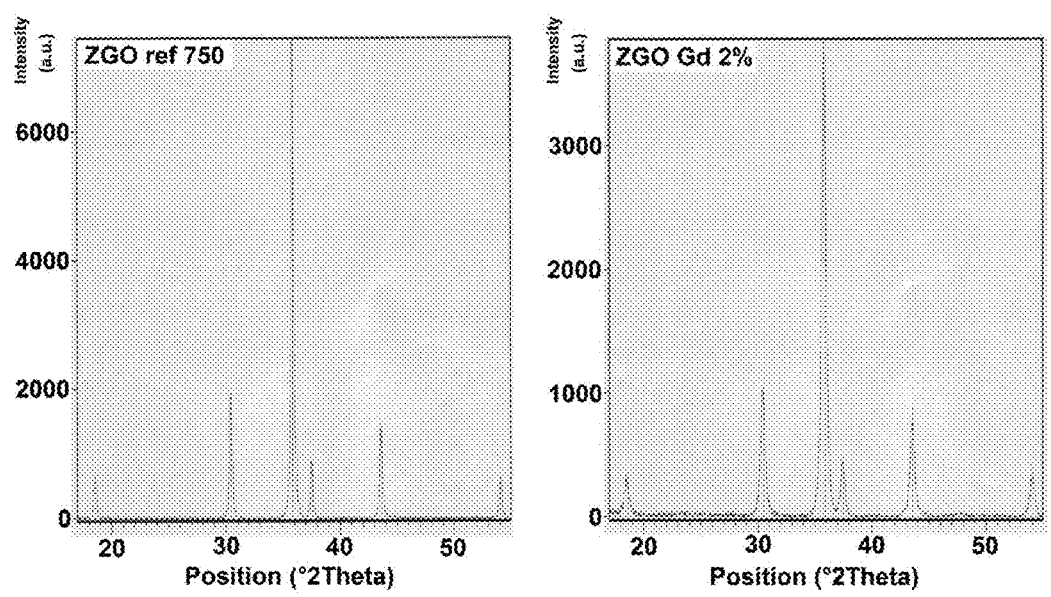

(51) Int. Cl.
  *A61K 49/18*  (2006.01)
  *A61B 5/055*  (2006.01)
  *C01G 15/00*  (2006.01)
  *A61B 90/00*  (2016.01)

(52) U.S. Cl.
  CPC ........ *A61K 49/0093* (2013.01); *A61K 49/186* (2013.01); *C01G 15/00* (2013.01); *C01G 15/006* (2013.01); *A61B 2090/3954* (2016.02); *C01P 2002/52* (2013.01); *C01P 2002/54* (2013.01); *C01P 2002/72* (2013.01); *C01P 2004/03* (2013.01); *C01P 2004/64* (2013.01); *C01P 2006/12* (2013.01); *C01P 2006/16* (2013.01); *C01P 2006/60* (2013.01); *C01P 2006/90* (2013.01)

(56) References Cited

OTHER PUBLICATIONS

Hilderbrand et al. "Near-infrared fluorescence: application to in vivo molecular imaging". Molecular Imaging. vol. 14, Issue 1, Feb. 2010, pp. 71-79.*

Le Masne de Chermont, Quentin, et al., "Nanoprobes with near-infrared persistent luminescence for in vivo imaging," Proceedings of the National Academy of Sciences of the United States of America 104, No. 22 (May 29, 2007): 9266-71.

Pan, Zhengwei, et al., "Sunlight-activated long-persistent luminescence in the near-infrared from Cr3+-doped zinc gallogermanates," Nature Materials 11, No. 1 (Nov. 20, 2011): 58-63. http://www.nature.com/doifinder/10.1038/nmat3173.

Bessière, Aurélie, et al., "ZnGa2 O4:Cr 3+ : a new red long-lasting phosphor with high brightness," Optics Express 19, No. 11 (2011): 10131-10137.

Liu, Yanlan, et al., "Fluorescence-enhanced gadolinium-doped zinc oxide quantum dots for magnetic resonance and fluorescence imaging." Biomaterials 32, No. 4 (Feb. 2011): 1185-92. http://www.ncbi.nlm.nih.gov/pubmed/21055806.

Kim, Jaeyun, et al., "Multifunctional Uniform Nanoparticles Composed of a Magnetite Nanocrystal Core and a Mesoporous Silica Shell for Magnetic Resonance and Fluorescence Imaging and for Drug Delivery," Inter Science, 2008, 8438-8441, http://doi.wiley.com/10.1002/ange.200802469.

Kang, Xiaojiao, et al., "Core-Shell Structured Up-Conversion Luminescent and Mesoporous NaYF4:Yb3+/Er3+@nSiO2@mSiO2 Nanospheres as Carriers for Drug Delivery," J. Phys. Chem. C 2011, 115, pp. 15801-15811.

Xu, Zhenhe, et al., "A luminescent and mesoporous core-shell structured Gd2O3: Eu3+@nSiO2@mSiO2 nanocomposite as a drug carrier." Dalton transactions (Cambridge, England: 2003) 40, No. 18 (May 14, 2011): 4846-54. http://www.ncbi.nlm.nih.gov/pubmed/21431226.

Jong Su Kim, et al., "Optical and Structural Properties of Nanosized ZnGa2O4:Cr3+ posphor," Solid State Communications 131 (2004) 735-738.

Dhak, P., et al., "Optical emission spectra of chromium doped nanocrystalline zinc gallate," Journal of Applied Physics 106, 063721-1 (2009), 6 pages.

Dec. 10, 2012 (FR) Search Report—App No. FR1250846.

May 27, 2013 (WO)—International Search Report—App. No. PCT/EP2013/051727.

Xie, Jin, et al., "Ultrasmall c(RGDyK)-Coated Fe3O4 Nanoparticles and Their Specific Targeting to Integrin ?v?3-Rich Tumor Cells," J Am Chem Soc. Jun. 18, 2008; 130(24): 7542-7543.

* cited by examiner

Small quantity of nanoparticles

Large quantity of nanoparticles

Liver

PERSISTENT LUMINESCENCE NANOPARTICLES EXCITABLE IN SITU FOR IN VIVO OPTICAL IMAGING, IN VIVO MULTIMODAL OPTICAL—MRI IMAGING, AND THERANOSTICS

RELATED APPLICATION DATA

This application is a National Stage Application under 35 U.S.C. 371 of co-pending PCT application PCT/EP2013/051727, designating the United States and filed Jan. 30, 2013; which claims the benefit of FR application number 1250846 and filed Jan. 30, 2012 each of which are hereby incorporated by reference in their entireties.

The subject of the invention concerns optical imaging methods whereby the persistent luminescence of nanoparticles is excited in vivo, after injection into a human or animal body, and is monitored in real time by the emitting of prolonged radiation in the near infra-red. The use of nanoparticles additionally having magnetic properties allows bimodal optical imaging—magnetic resonance imaging (MRI). In addition, these nanoparticles when coated with a layer of mesoporous silica have the capability of loading and releasing molecules of interest which may find applications in theranostics.

Most optical systems used for diagnosis available on the marked are based on fluorescence phenomena which require continuous excitation of the probe. However, this excitation is the cause of a parasitic signal from animal tissue: autofluorescence responsible for a significant drop in sensitivity at the time of detection.

International application WO2007/048856 and application FR 2 908 891 describe persistent luminescence nanoparticles and the use thereof as in vivo diagnosis agents. Excitation of the nanoparticles is obtained in vitro before injection, via irradiation under a UV lamp. Once injected into an animal these nanoparticles can be monitored for several tens of minutes through the animal body but any observation over a time of more than 60 minutes is inoperative on account of the short lifetime of the luminescent signal and the impossibility of exciting the nanoparticles through the animal body after injection.

Kim et al. (2004) have described the preparing of nanoparticles of type $ZnGa_2O_4:Cr^{3+}$ and their optical photoluminescence properties, but do not report any property of persistent luminescence. Applications in the field of high definition television are envisaged. More recently Bessière et al. (2011) have shown that this same material in micrometric form has persistent luminescence properties which can be excited in the UV at 254 nm. Pan et al. (2012) have described the persistent luminescence properties of a gallogermanate of formula $Zn_3Ga_2Ge_2O_{10}:Cr^{3+}$ having a crystal size of between 2 and 5 µm, and propose the use thereof as night-time marker in the field of solar energy storage and in the diagnostic methods described by Le Masne de Chermont et al. (2007) wherein the nanomaterials are excited before being injected into an animal body.

With the present invention it is possible to overcome an essential limitation of first generation persistent luminescence nanoparticles in that excitation thereof is possible in vivo through animal tissue. Although in vitro excitation under UV is still possible, the nanoparticles used in the optical imaging methods of the present invention have the capability of being excited in the visible wavelength regions between 550 and 800 nm and more particularly between 550 and 650 nm. These orange-red photons relatively close to the transparency window of tissues prove to be sufficiently penetrating to allow excitation of the persistent luminescence of nanoparticles in vivo, through an animal body. In this manner observation avoids any time constraints and the nanoparticles can be located for as long as crystal integrity is maintained. In addition, it is then possible to monitor their degradation kinetics via non-invasive optical imaging.

This new generation of persistent luminescence nanoparticles has the advantage of very strong signal-to-noise ratio and absolute contrast through the absence of autofluorescence. However the scattering phenomena encountered in optical imaging sometimes lead to imprecise locating of nanoparticles within the body observed in vivo. This technical problem is overcome by the addition of another modality: magnetic resonance imaging which allows precise locating of the probe in the organ of interest.

The addition of a paramagnetic cation in the structure of these nanomaterials allows the providing of an additional imaging modality, MRI, without affecting the initial persistent luminescence properties or the capability of the nanoparticles to be excited through animal tissue. This nanomaterial has the same optical properties as those described above and also has magnetic properties of interest allowing the use thereof as contrast agent for MRI (T2 effect, negative contrast).

The invention also offers the possibility of encapsulating the persistent luminescence nanoparticles in a mesoporous silica shell to allow the loading and release of molecules of interest. In particular this multifunctional system, via the persistent luminescence phenomenon, can allow the locating of the release regions of an active ingredient or cytotoxic molecule, and thereby provide better control over the administering of a drug through real-time monitoring of its location in the body.

These nanoparticles and methods find numerous applications in the field of medical imaging, diagnosis and therapy.

SUMMARY

The subject of the invention pertains to persistent luminescence nanoparticles, said nanoparticles emitting photons at wavelengths of between 550 and 1000 nm for at least 0.01 second, after excitation under light at wavelengths of between 550 and 1000 nm, for use thereof as optical probes in a diagnosis method via in vivo optical imaging of a human or animal body, comprising the following steps:
   a) Administering the nanoparticles to the human or animal body;
   b) Exciting the persistent luminescence of the nanoparticles by in vivo irradiation under a wavelength between 550 and 1000 nm in all or part of the human or animal body; and
   c) Detecting the nanoparticles in vivo in all or part of the human or
   animal body by measuring the persistent luminescence of the nanoparticles via optical imaging.

In preferred embodiments, the nanoparticles comprise a nanomaterial formed of a matrix selected from among gallates, aluminates, indates, and their mixed compounds gallo-germanates, gallo-aluminates, gallo-indates, gallium oxides, indium oxides, magnesium oxides, zinc and gallium oxysulfides, zinc and gallium oxyselenides, zinc and gallium oxytellurides, said matrix being doped with a transition metal or a lanthanide selected from among chromium, europium, cerium, nickel, iron, copper and cobalt.

Preferably the nanoparticles comprise the nanomaterial $ZnGa_{2(1-x)}Cr_{2x}O_4$ with x being between 0.001 and 0.0075. More preferably the nanoparticles comprise the nanomaterial $ZnGa_{1.995}Cr_{0.005}O_4$.

Preferably, the administration of the nanoparticles is performed via intravenous, intra-arterial, intramuscular, intraperitoneal or retro-orbital route.

Preferably the size of the nanoparticles is between 1 and $10^3$ nm.

In preferred embodiments, the nanoparticles are surface grafted or coated.

In a first embodiment, the nanoparticles are grafted on the surface with a ligand. In another embodiment, the nanoparticles are encapsulated in mesoporous silica allowing the loading and release of molecules of interest.

A further subject of the invention is persistent luminescence nanoparticles, said nanoparticles emitting photons at wavelengths of between 550-1000 nm for at least 0.01 second, after excitation under light at wavelengths of between 550 and 1000 nm and said nanoparticles having paramagnetic properties, for use thereof as optical probes in a diagnosis method using in bimodal in vivo imaging of a human or animal body, comprising the following steps:
  a) Administering the nanoparticles to the human or animal body;
  b) Exciting the persistent luminescence of the nanoparticles by in vivo irradiation under a wavelength between 550 and 1000 nm of all or part of the human or animal body;
  c) Detecting the nanoparticles in vivo in all or part of the human or animal body, by measuring the persistent luminescence of the nanoparticles by optical imaging; and
  d) Detecting the nanoparticles in vivo in all or part of the human or animal body by magnetic resonance imaging.

In preferred embodiments, the nanoparticles comprise a nanomaterial formed of a matrix selected from gallates, aluminates, indates, gallium oxides, indium oxides, magnesium oxides, gallo-germanates, alumino-gallates, zinc and gallium oxysulfides, zinc and gallium oxyselenides, zinc and gallium oxytellurides, said matrix being doped with a transition metal or lanthanide selected from among chromium, europium, cerium, nickel, iron, copper and cobalt, and at least one paramagnetic element selected from among $Cr^{3+}$; $Mn^{2+}$; $Gd^{3+}$; $Fe^{3+}$ and $Ni^{3+}$.

Preferably the nanoparticles comprise a nanomaterial $ZnGa_{2(1-x-y)}Cr_{2x}Gd_{2y}O_4$ with x between 0.001 and 0.0075 and y between 0.01 and 0.08. More preferably, the nanoparticles comprise the nanomaterial $ZnGa_{1.955}Cr_{0.005}Gd_{0.04}O_4$.

Preferably, the administering of the nanoparticles is performed via intravenous, intra-arterial, intramuscular, intraperitoneal or retro-orbital route.

Preferably the nanoparticles have a size of between 1 and $10^3$ nm.

In preferred embodiments, the nanoparticles are surface grafted or coated.

In a first embodiment, the nanoparticles are grafted on the surface with a ligand. In another embodiment, the nanoparticles are encapsulated in mesoporous silica allowing the loading and release of molecules of interest.

The invention relates to nanoparticles comprising the nanomaterial $ZnGa_{2(1-x-y)}Cr_{2x}Gd_{2y}O_4$ with x between 0.001 and 0.0075 and y between 0.01 and 0.08.

Preferably the nanoparticles comprise the nanomaterial $ZnGa_{1.955}Cr_{0.005}Gd_{0.04}O_4$.

The size of the nanoparticles is preferably between 1 and $10^3$ nm.

DESCRIPTION OF THE INVENTION

According to a first aspect, the invention relates to persistent luminescence nanoparticles emitting photons at wavelengths of between 550-1000 nm for at least 0.01 second after excitation under light at wavelengths of between 550 and 1000 nm, for use thereof as optical probes in a diagnosis method using in vivo optical imaging of a human or animal body, comprising the following steps:
  a) Administering the nanoparticles to the human or animal body;
  b) Exciting the persistent luminescence of the nanoparticles by in vivo irradiation, under a wavelength of between 550 and 1000 nm, of all or part of the human or animal body; and
  c) Detecting the nanoparticles in vivo in all or part of the human or animal body by measuring the persistent luminescence of the nanoparticles via optical imaging.

A further subject of the invention concerns in vivo optical imaging methods of a human or animal body comprising the following steps:
  a) Administering said nanoparticles to the human or animal body, said nanoparticles emitting photons at wavelengths between 550 and 1000 nm for at least 0.01 second, after excitation under light at wavelengths between 550 and 1000 nm;
  b) Exciting the persistent luminescence of the nanoparticles by in vivo irradiation of all or part of the human or animal body under a wavelength between 550 and 1000 nm; and
  c) Detecting the nanoparticles in vivo in all or part of the human or animal body by measuring the persistent luminescence of the nanoparticles via optical imaging.

The invention also pertains to in vivo optical imaging methods of a human or animal body comprising the following steps:
  b) Exciting the persistent luminescence of nanoparticles by in vivo irradiation of all or part of the human or animal body under a wavelength of between 550 and 1000 nm, said nanoparticles being previously administered to the human or animal body, and said nanoparticles emitting photons at wavelengths between 550 and 1000 nm for at least 0.01 second, after light excitation at wavelengths between 550 and 1000 nm; and
  c) Detecting the nanoparticles in vivo in all or part of the human or animal body by measuring the persistent luminescence of the nanoparticles via optical imaging.

In particular embodiments of the invention, the use of nanomaterials having both persistent luminescence properties after excitation in the visible range between 550-1000 nm and paramagnetic properties allows the use of two imaging modalities, optical imaging and MRI for in vivo detection of the nanoparticles.

A further subject of the invention concerns persistent luminescence nanoparticles, said nanoparticles emitting photons at wavelengths between 550-1000 nm for at least 0.01 second, after light excitation at wavelengths between 550 and 1000 nm, and said nanoparticles having paramagnetic properties, for use thereof as optical probes in a diagnosis method using bimodal in vivo imaging of a human or animal body, comprising the following steps:
  a) Administering the nanoparticles to the human or animal body;

b) Exciting the persistent luminescence of the nanoparticles by in vivo irradiation of all or part of the human or animal body under a wavelength between 550 and 1000 nm;

c) Detecting the nanoparticles in vivo in all or part of the human or animal body by measuring the persistent luminescence of the nanoparticles via optical imaging; and d) Detecting the nanoparticles in vivo in all or part of the human or animal body by magnetic resonance imaging.

The invention also concerns bimodal in vivo imaging methods of a human or animal body, comprising the following steps:

a) Administering nanoparticles to the human or animal body, said nanoparticles emitting photons at wavelengths between 550-1000 nm for at least 0.01 second, after excitation under light at wavelengths between 550 and 1000 nm and said nanoparticles having paramagnetic properties;

b) Exciting the persistent luminescence of the nanoparticles by in vivo irradiation of all or part of the human or animal body under a wavelength of between 550 and 1000 nm;

c) Detecting the nanoparticles in vivo in all or part of the human or animal body by measuring the persistent luminescence of the nanoparticles via optical imaging; and d) Detecting the nanoparticles in vivo in all or part of the human or animal body by magnetic resonance imaging.

The invention also concerns bimodal in vivo imaging methods of a human or animal body comprising the following steps:

a) Exciting the persistent luminescence of nanoparticles by in vivo irradiation of all or part of the human or animal body under wavelengths between 550 and 1000 nm, said nanoparticles being previously administered to the human or animal body, and said nanoparticles emitting photons at wavelengths between 550-1000 nm for at least 0.01 second, after light excitation at wavelengths between 550 and 1000 nm and said nanoparticles having paramagnetic properties;

b) Detecting the nanoparticles in vivo in all or part of the human or animal body by measuring the persistent luminescence of the nanoparticles via optical imaging; and c) Detecting the nanoparticles in vivo in all or part of the human or animal body by magnetic resonance imaging.

Numerous nanomaterials and their optical properties have been described in the literature including nanomaterials in particular having persistent luminescence properties.

Luminescence is the generic term to characterize substances which restore part of the energy absorbed during non-thermal excitation in the form of photons of non-thermal origin. The excitation of these compounds is obtained by providing energy which may adopt numerous forms. Mention can be made, without this list being exhaustive, of excitation by wavelengths in the ultraviolet (UV), visible or infrared range (IR), X-rays, chemical reactions (chemiluminescence), enzymatic reactions (bioluminescence), electric excitation (electroluminescence) or mechanical excitation (triboluminescence).

The nanoparticles of the present invention are chosen for their persistent luminescence properties at wavelength ranges allowing both excitation of luminescence and the detection of luminescence through the tissue of a human or animal body.

The nanoparticles of the present invention emit photons at wavelengths between 550 and 1000 nm after light excitation at wavelengths between 550 and 1000 nm. Preferably the nanoparticles emit photons after excitation at wavelengths between 550 and 800 nm and more preferably between 550 and 650 nm.

The emitted photons preferably have a wavelength in the near infrared and particularly in the region of 700 nm.

The nanoparticles of the invention emit photons for at least 0.01 second. Preferably the nanoparticles emit photons for at least 1 second, advantageously for at least 1 minute, 30 minutes, 1 hour, even at least 10 hours. The persistence times are evaluated by monitoring the intensity of luminescence as a function of time after excitation. Clear comparisons of persistence time measurements must be made under identical conditions using the same detection systems. The expression "persistent luminescence nanomaterial" is applied to nanomaterials having luminescence of at least 0.01 second and up to several hours even several days.

The nanoparticles emitting photons for less than 0.01 second are not included in the present invention since this would relate to fluorescence and is distinct from persistent luminescence.

In the present application by "nanoparticle" it is meant to designate a particle whose size is defined such that the longest dimension along an axis is generally between 1 and 1000 nm and more particularly between 10 and 1000 nm. Preferably the nanoparticle of the invention is between 20 nm and 1000 nm, more preferably between 20 nm and 200 nm.

Preferably the nanoparticle is formed of a matrix nanomaterial selected from among:

gallates, aluminates, indates;

oxysulfides, oxyselenides and oxytellurides of zinc/magnesium and gallium/aluminium/indium;

gallium oxides, indium oxides, magnesium oxides and their corresponding mixed oxides;

mixed compounds such as gallo-germanates, alumina-gallates;

Preferably, the gallates are selected from among $Zn_xMg_{(1-x)}Ga_2O_4$ with x between 0 and 1, $LiGa_5O_8$ and $Ln_3Ga_5O_{12}$ (Ln=Y, Gd, La or Lu).

Preferably, the aluminates are selected from among $Zn_xMg_{(1-x)}Al_2O_4$ with x between 0 and 1.

Preferably, the indates are selected from among $Zn_xMg_{(1-x)}In_2O_4$ with x between 0 and 1.

Preferably the oxides are selected from among $Ga_2O_3$, $In_2O_3$ and $MgO$.

Preferably, the gallo-germanates are selected from among $M_3Ga_2Ge_4O_{14}$ (M=Sr, Ca), $Zn_xGa_yGe_zO_{(x+(3y/2)+2z)}$ with x, y and z integers from 1 to 5 and $La_3Ga_5GeO_{14}$.

Preferably, the alumina-gallates are selected from among $Zn_xMg_{(1-x)}(Ga_{1-y}Al_y)_2O_4$ with x between 0 and 1, and y strictly between 0 and 1 (these two values being excluded).

Other hybrid compounds are selected for example from among $Zn_xMg_{(1-x)}(Ga_{1-y}In_y)_2O_4$ with x between 0 and 1, and y strictly between 0 and 1 (these two values being excluded); $La_3Ga_5SiO_{14}$ and $La_3Ga_{5.5}Nb_{0.5}O_{14}$.

These matrixes are doped with a transition metal or lanthanide, preferably selected from among chromium, europium, cerium, nickel, iron, copper and cobalt.

The nanomaterials may also comprise co-dopants to improve the luminescence properties of these structures such as $Li^+$; $Na^+$ and $Ag^+$.

The nanomaterials may comprise any other suitable co-dopant.

To impart magnetic properties to the nanoparticles, the matrixes are doped with at least one paramagnetic element selected from among $Cr^{3+}$, $Mn^{2+}$, $Gd^{3+}$, $Fe^{3+}$ and $Ni^{3+}$.

One preferred nanomaterial is $ZnGa_{2(1-x)}Cr_{2x}O_4$ with x between 0.001 and 0.0075 and more preferably $ZnGa_{1.995}Cr_{0.005}O_4$.

Another preferred nanomaterial is $Zn_3Ga_2Ge_2O_{10}$:0.5% $Cr^{3+}$.

Among the nanomaterials allowing bimodal optical and MRI imaging, one preferred nanomaterial is $ZnGa_{2(1-x-y)}Cr_{2x}Gd_{2y}O_4$ with x between 0.001 and 0.0075 and y between 0.01 and 0.08, and more preferably $ZnGa_{1.955}Cr_{0.005}Gd_{0.04}O_4$.

This list of nanomaterials is non-limiting and it is within the reach of persons skilled in the art to determine which persistent luminescence materials can be used in the present invention.

The invention also relates to nanoparticles comprising the above-described nanoparticles and dopants.

In one embodiment, the nanoparticles of the invention are for therapeutic use.

In preferred embodiments, the nanoparticles of the invention are used as optical probes or markers for in vivo optical imaging in a human or animal body. The animal body is preferably a mammal, and more preferably a small mammal such as a mouse, rat, rabbit or guinea pig.

The nanoparticles and imaging methods of the invention are particularly adapted for imaging the vascular network of a human or animal body.

The administering of nanoparticles to the human or animal body can be carried out using any suitable technique. Preferably, administration is given via intravenous, intra-arterial, intramuscular, intraperitoneal or retro-orbital route. In the present invention and contrary to the prior art, it is not necessary to excite the persistent luminescence of the nanoparticles prior to their injection into the human or animal body.

The nanoparticles and the imaging methods of the present invention are based on excitation of the nanoparticles a in situ H, after injection into the human or animal body. It therefore becomes possible to repeat this excitation at will over time and to perform true real-time tracking of the distribution and locating of the nanoparticles in the human or animal body up until altered integrity of the nanoparticles.

The excitation of the nanoparticles is conducted in the visible range at a wavelength between 550 and 1000 nm and preferably between 550 and 800 nm, more preferably between 550 and 650 nm. Unexpectedly, these photons, relatively close to the transparency window of tissues, prove to be sufficiently penetrating to allow sufficient excitation of the nanoparticles in vivo though the human or animal body. In addition, no autofluorescence phenomenon is observed so that the signal-to-noise ratio is most favourable and the contrast obtained when imaging is of good quality.

This excitation is therefore performed by in vivo irradiation of all or part of the human or animal body. The human or animal body is subjected for example to a light-emitting diode or a halogen for a few minutes.

By means of their persistent luminescence property, the nanoparticles are detected in vivo through the tissues of the human or animal body by optical imaging using a suitable optical detector (ICCD camera for example).

When the nanoparticles have magnetic or paramagnetic properties, they can also be used in magnetic resonance imaging (MRI). The nanoparticles then act as contrast agent. It subsequently becomes possible to detect the nanoparticles in vivo in the human or animal body by bimodal imaging combining optical imaging and MRI.

According to preferred embodiments of the invention the nanoparticle excitation step, followed by the steps of nanoparticle detection by measuring persistent luminescence under optical imaging and optionally also under MRI imaging, can be repeated in vivo in all or part of the human or animal body. After full or partial extinction of the persistent luminescence of the nanoparticles, it becomes possible to re-excite this luminescence thereby entirely overcoming the constraints related to the duration of this luminescence and the loss of intensity of luminescence over time.

The nanoparticles and the imaging methods of the invention therefore allow real-time monitoring of the nanoparticles in the human or animal body and for several hours and even several days.

This opens up a vast field of new applications since it is henceforth possible, after injection, to track the distribution and locating of the nanoparticles in the human or animal body in vivo and in real time.

In general, the nanoparticles of the invention can be administered to the human or animal body without any additional treatment of the nanomaterial.

According to particular embodiments, the nanoparticles can be coated, functionalised and/or encapsulated for example. These operations are performed using usual techniques known to those skilled in the art.

It may be important to be able to modify the surface condition of the nanoparticles to promote their circulation within the human or animal body. In particular, it may be advantageous to mask the ionic charges on the surface of the particles by means of a coating to promote the circulation of the nanoparticles after systemic injection.

According to one particular embodiment, the nanoparticle of the invention is functionalised by coating with a chemical molecule, a polymer, by grafting a substance of biological or chemical interest, and/or by grafting a ligand allowing in vivo binding with a receptor or substance of biological or chemical interest in the human or animal body.

By grafting a ligand of biological receptors or substances of biological interest on the surface of the nanoparticles, it is possible to target the nanoparticles onto an organ, a tissue or particular cells of the human or animal body. This may be of interest both for diagnosis and for therapeutic purposes.

The substance of interest may be a chemical molecule known for example for its affinity for some cell receptors. It may also be an antibody, a protein or nucleic acid. The terms protein, polypeptide or peptide indifferently designate an amino acid sequence, such as the RGD or PHSCN peptides known for their strong affinity for some integrins overexpressed in several forms of cancer, or the derivatives thereof, for example a compound containing an amino acid sequence. Similarly, the terms nucleic acid, nucleic sequence or nucleic acid sequence, polynucleotide, oligonucleotide, polynucleotide sequence, nucleotide sequence are used indifferently to designate precise sequencing of nucleotides, whether or not modified, allowing the deigning of a fragment or region of a nucleic acid, whether or not comprising non-natural nucleotides, and possibly corresponding both to a small interfering RNA (<<siRNA>>), double strand DNA, single strand DNA and to transcription products of said DNAs. These nucleic acids are isolated from their natural environment, and are natural or artificial.

The substance of interest may in particular be an active ingredient or a therapeutic molecule.

To control the biodistribution of persistent luminescence nanoparticles and to guide them towards a substance of biological or chemical interest in a body or tissue, their surface must be functionalised by coating and/or grafting a ligand capable of binding to the substance which may be present in the tissue of the organ of interest.

Coating methods are well known to persons skilled in the art. For example, coating can be performed by binding with molecules carrying phosphate, carboxylate or thiol groups, or by hetero-precipitation of silica, aminosilane or preferably triethoxyaminopropylsilane. Coating performed with triethoxyaminopropylsilane has the advantage of only forming a single layer, without outer polymerisation, thereby limiting the increase in the diameter of the nanoparticles.

Similarly ligand grafting (or coupling) methods are well known to skilled persons. This generally concerns coupling by covalent bonding via affinity, passive or forced adsorption. For coupling via covalent bonding, the nanoparticles are carriers of chemical groups capable of reacting with another chemical group carried by the ligand to form a covalent bond. As examples of chemical groups which can be present on the surface of the nanoparticles, carboxylic acids, amines, aldehydes and epoxy can be cited but are not limited thereto. It is also possible to use interaction via affinity, which is generally performed using two partners of a binding pair having high affinity such as the pairs (poly) carbohydrate/lectin, biotin or biotinylated compounds/avidin or streptavidin, receptor/specific ligand, antigen or hapten/antibody, etc.

The grafting of nanoparticles can be conducted directly using spacer arms also called linkers or spacers.

Coupling by passive or forced adsorption is known to skilled persons. For example use can be made of biotin-BSA (Bovin Serum Albumin).

Coating can be obtained by encapsulating the nanoparticle in a non-viral synthetic vector such as liposomes, lipoplexes or any other soft lipid structure.

Preferably coating is performed by surface precipitation of triethoxy aminopropylsilane, by polymerisation of monomers or adsorption of polymers on the surface of the nanoparticles.

According to another preferred embodiment, polyethylene glycol (PEG) is grafted for stealth purposes (to extend the circulation time in the body). In general, procedure is as follows: the PEG is first coupled with the ligand and the coupled product is grafted on the nanoparticle.

Coating or surface grafting of the nanoparticles may also have the advantage of masking the ion charges on the surface of the particles.

Further preferably the nanoparticle of the invention is functionalised by surface precipitation of triethoxyaminopropylsilane followed by grafting of methoxy-$PEG_x$-COOH (x between 0.2 and 20 kDa) allowing binding with the substance of biological or chemical interest.

In addition, toluene can be replaced by dimethylformamide, thereby allowing better dispersion of the particles. The particles can be functionalised by carboxylate groups (by reaction of diglycolic anhydride on the amino particles) but also by thiol groups after direct reaction with 3-mercaptopropyl-triethoxysilane. The grafting of polyethylene glycol (PEG) can be performed directly by peptide coupling. It is also possible to graft different chemical molecules on the surface of the nanoparticles (biotin, peptide).

According to one preferred embodiment, the nanoparticle of the invention is functionalised by carboxylate, thiol or free amine groups.

The nanoparticles of the invention can also be used as optical probes or markers to tag macromolecules or cells before injection into a human or animal body. The in vivo distribution in real time of the molecules tagged with the nanoparticles is monitored by optical imaging and optionally also by MRI imaging.

The real time in vivo optical imaging of macrophages tagged with nanoparticles of the invention is described in the examples.

The nanoparticles of the invention can therefore be used to tag cells and track their location and distribution in vivo over time after injection thereof into a human or animal body. Various applications can therefore be envisaged in the field of cell therapy for example and in particular in clinical trials to follow the outcome of injected cells.

In other embodiments the nanoparticles of the invention can be encapsulated in a mesoporous silica shell in accordance with techniques described in the literature. Nanoparticles having a said mesoporous silica casing and their methods of preparation are described for example by Kang et al. (2011), Kim et al. (2008) and Xu et al. (2011).

The mesoporous silica surrounding the nanoparticles does not affect their persistent luminescence properties or their possible paramagnetic properties. This porous layer allows the loading and release of substances of biological or chemical interest.

The substance of interest may be a chemical molecule for example such as an active ingredient, a therapeutic molecule or a cytotoxic substance. It may also be a hormone, a protein, a nucleic acid. The terms protein, polypeptide or peptide indifferently designate an amino acid sequence or, for the derivatives thereof, a compound containing an amino acid sequence. Similarly, the terms nucleic acid, nucleic sequence or nucleic acid sequence, polynucleotide, oligonucleotide, polynucleotide sequence, nucleotide sequence are used indifferently to designate precise sequencing of nucleotides, whether or not modified, allowing the defining of a fragment or region of a nucleic acid which may or may not comprise non-natural nucleotides and possibly corresponding both to a small interfering RNA (<<<siRNA>>), double strand DNA, single strand DNA, and to transcription products of said DNA or RNA. These nucleic acids isolated from their natural environment, and are natural or artificial.

The nanoparticles therefore find numerous applications in diagnosis, therapy and theranostics.

Vascular imaging is of interest for example for evidencing angiogenic processes in chronic inflammation, tumour growth or the locating of metastases. Biodistribution studies are essential for determining the accumulation ratios of an agent that is or is not vectored by particular forms at the target tissues. Further preferably, the diagnosis agent is intended for the imaging of tumoral, inflammatory regions of the retina, said regions likely to be hyper-vascularised, or rupture regions of the blood-brain barrier. According to another embodiment the diagnosis agent is intended for imaging hypo-vascularised regions e.g. in the case of cerebral or cardiac ischemia or head injury. A further use is the in vivo detection of inflammatory or tumoral regions which are hyper-vascularised regions. One particular application is therefore the early detection of cancer.

According to another embodiment, the diagnosis agent allows mimicking of the biodistribution of liposomes or nanovectors in vivo as part of gene therapy strategy.

In general, the invention is intended in particular for the field of biological, medical and clinical research as optical probe or multimodal probe having simultaneous properties of optical marker and MRI contrast agent. The examples report one application of these optical probes for real-time in vivo cell monitoring in a human or animal body. The nanoparticles can therefore be used as cell markers for real-time tracking of the biodistribution of some cell types. These techniques also allow the optical visualisation of graft healing in cell therapy which is of increasing interest within scientific and medical circles.

Through their unique persistent luminescence properties these nanoparticles also open up the field to per-operative applications to assist surgeons in tumour excision. In this precise case, the nanoparticles can be used as tumour cell markers thereby increasing their metabolism and endocytosis capacity, to guide and facilitate excision of metastases and tumour sites in some cancers, in particular breast and bladder tumours.

The presence of a mesoporous layer around the persistent luminescence nanoparticle opens up the field to other applications, theranostics in particular, other functions or even other imaging modalities. The nanoparticles and methods of the invention allow the observation/diagnosis and joint treatment (theranostic) of pathologies, or allow monitoring of the efficacy of treatment via optical imaging.

According to one particular embodiment, the subject of the present invention concerns nanoparticles such as previously defined for use thereof as diagnostic agent intended for in vivo optical imaging.

FIGURES

FIG. 1: Diffractogram of $ZnGa_{1.995}Cr_{0.005}O_4$ (left) and $ZnGa_{1.955}Cr_{0.005}Gd_{0.04}O_4$ (right) compounds. The vertical lines indicate the reference diffraction peaks of $ZnGa_2O_4$ (reference code: 00-038-1240).

Figure 2:
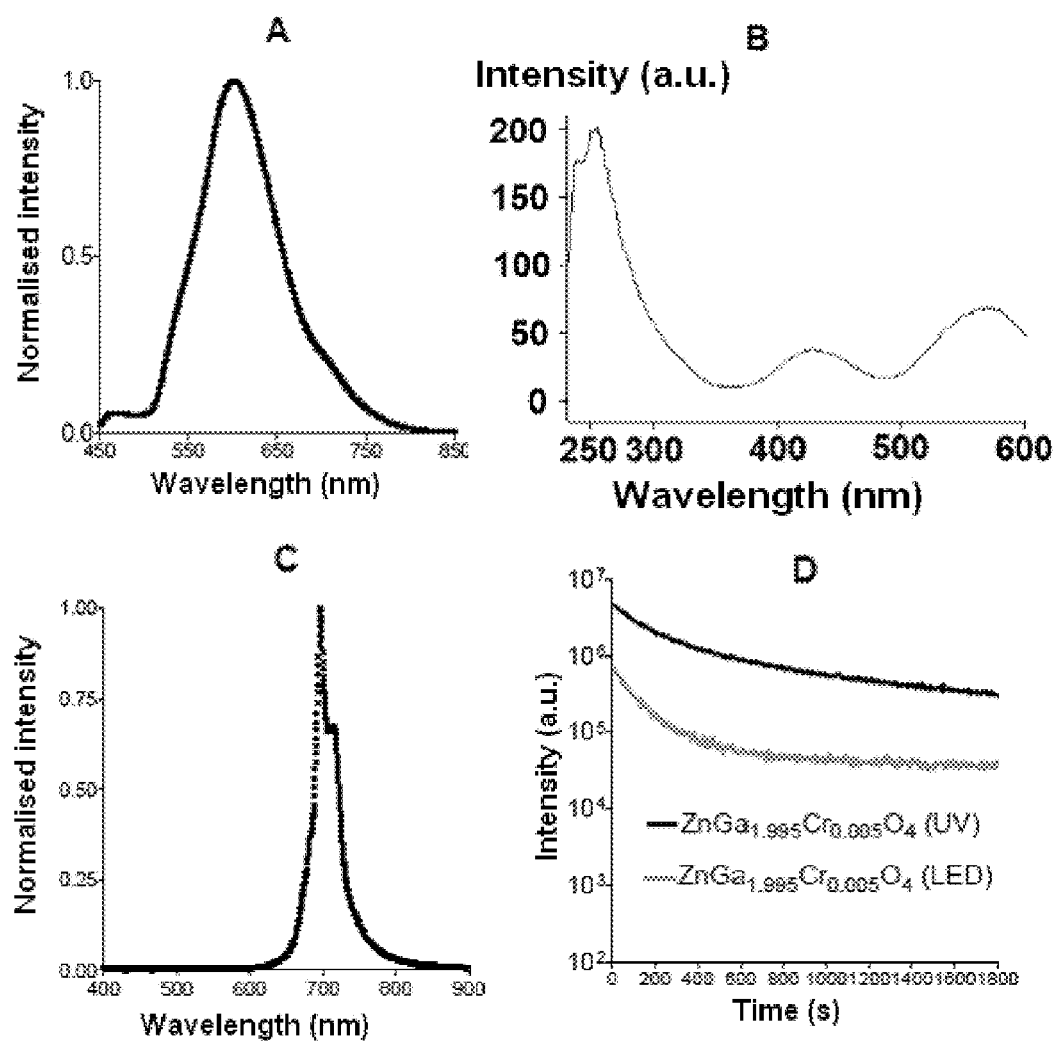

FIG. 2: Emission spectrum of LED lamp used for visible range excitation (orange-red) of the nanoparticles (A). Excitation spectrum of photoluminescence at 705 nm of the compound $ZnGa_{1.995}Cr_{0.005}O_4$ (B). Emission spectrum of persistent luminescence after UV and visible excitation (C). Compared decay of persistent luminescence after UV excitation or using the LED system (D).

Figure 3:
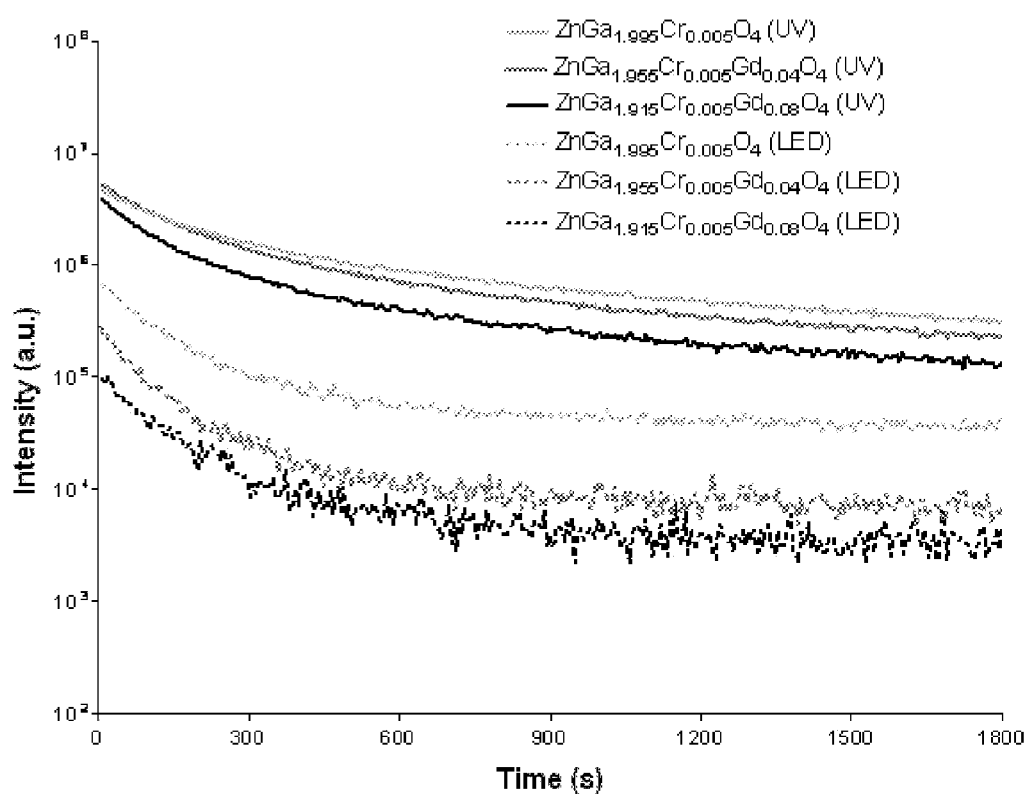

FIG. 3: Compared decay of persistent luminescence according to material composition and type of excitation.

Figure 4:
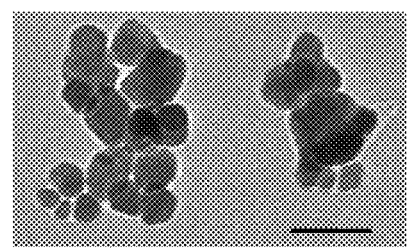

FIG. 4: Electron microscope image of nanoparticles of $ZnGa_{1.995}Cr_{0.005}O_4$ (the bold line represents 80 nm).

Figure 5:
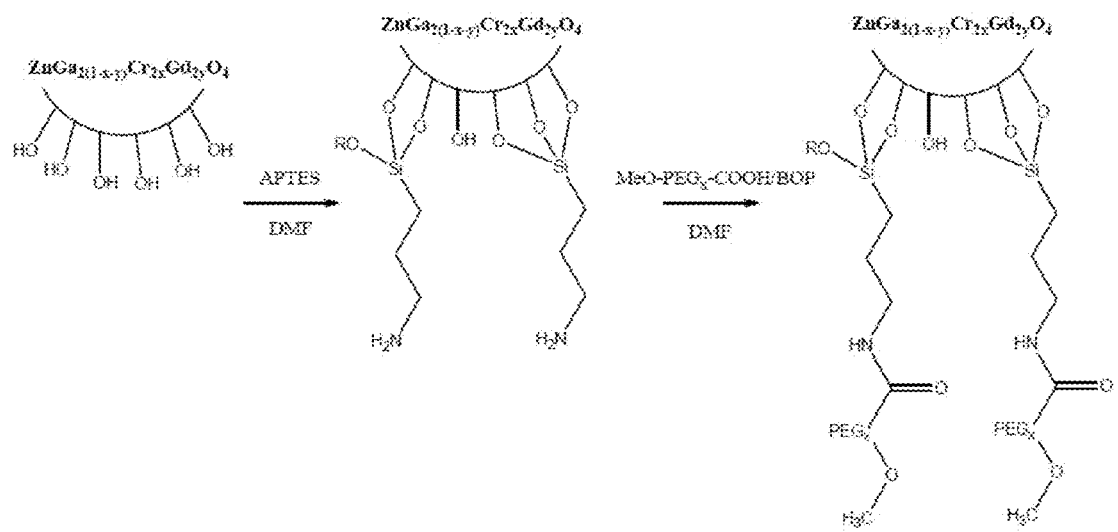

FIG. 5: Functionalization scheme of $ZnGa_{2(1-x-y)}Cr_{2x}Gd_{2y}O_4$ nanoparticles.

Figure 6:
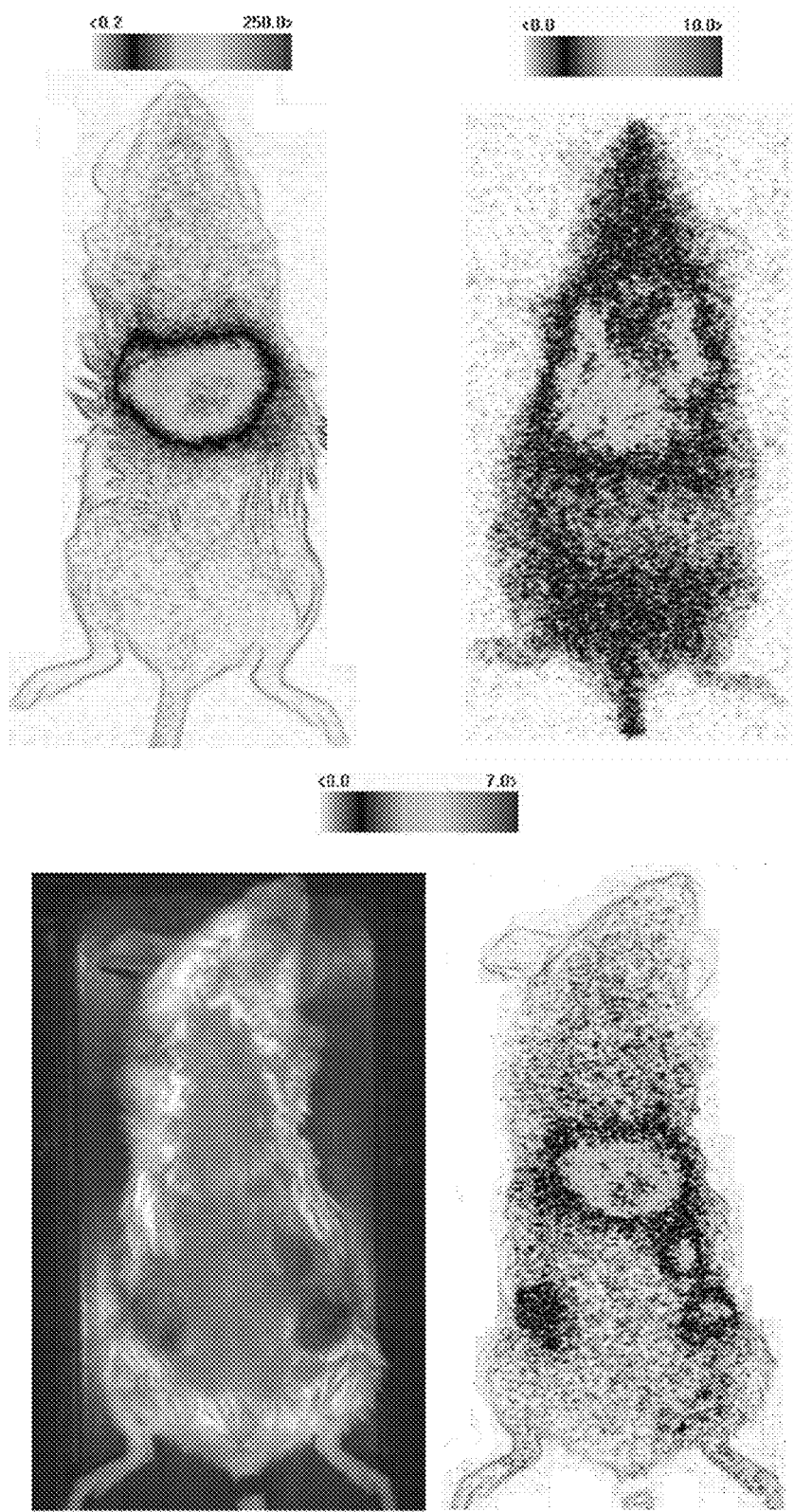

FIG. 6: Top picture: On the left, mouse injected with hydroxylated particles (negative charge). On the right, mouse injected with PEGylated particles (neutral). Bottom pictures: On the left, optical image of a mouse carrying three sub-cutaneous CT26 tumours and injected (intravenous) with nanoparticles of $ZnGa_{1.995}Cr_{0.005}O_4$. On the right, persistent luminescence signal obtained after illumination of the animal under an orange-red light source (see FIG. 2.A), 4 hours after injection of the probe.

Figure 7:
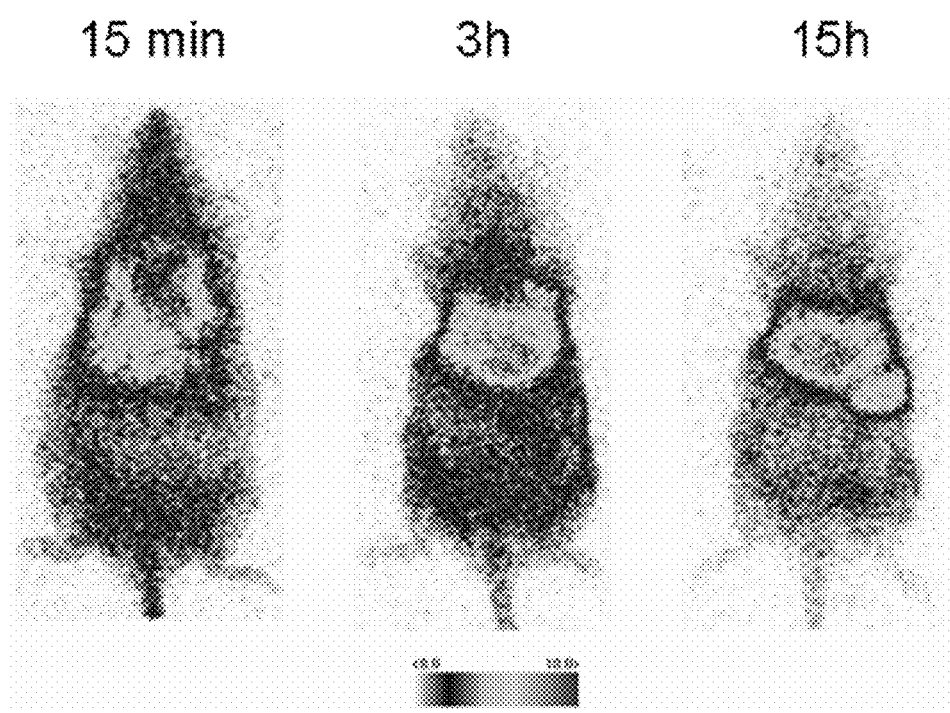

FIG. 7: In vivo images of the biodistribution of stealth nanoparticles at different times. The mouse was injected with 2 mg of PEGylated nanoparticles having a core diameter of 80 nm. Long-length times are accessible via re-excitation of the persistent luminescence of the particles for 2 minutes under an orange-red light source (see FIG. 2.A) through animal tissue.

Figure 8:
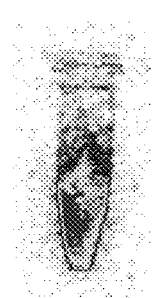
Figure 8:
Figure 8:
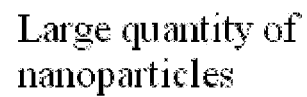

FIG. 8: Acquisition under persistent luminescence of the signal from a suspension of RAW macrophages tagged with persistent luminescence nanoparticles.

Figure 9:
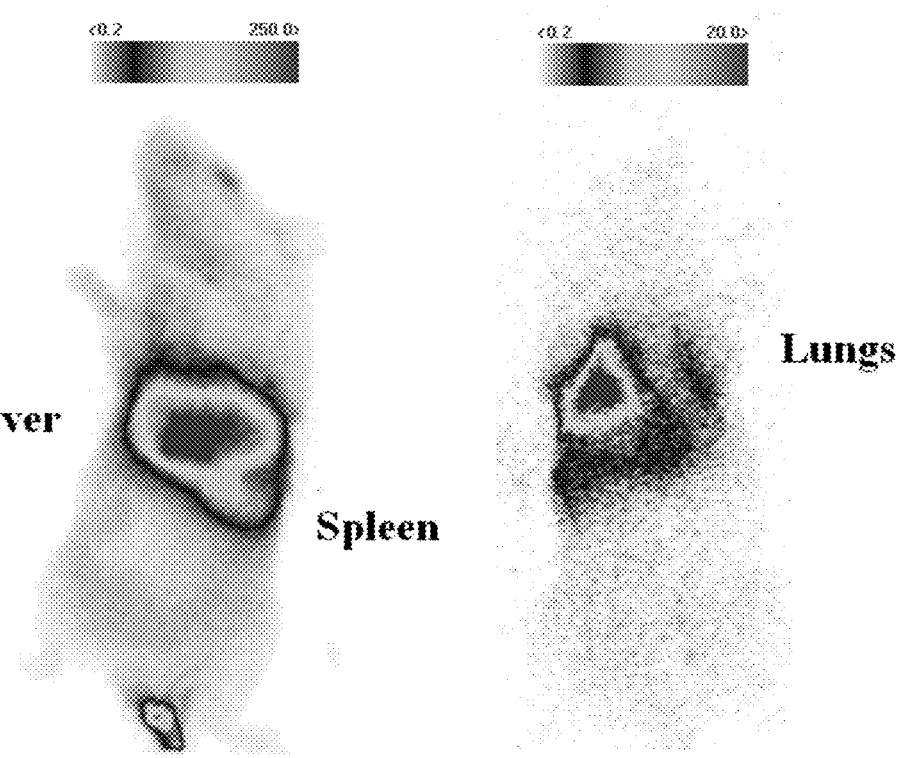

FIG. 9: Compared in vivo biodistribution 30 minutes after systemic injection of amino persistent luminescence nanoparticles (left) and RAW cells (murine macrophages) tagged with the same persistent luminescence particles (right). These images were recorded after excitation of persistent luminescence in the visible range (between 550 and 700 nm).

Figure 10:
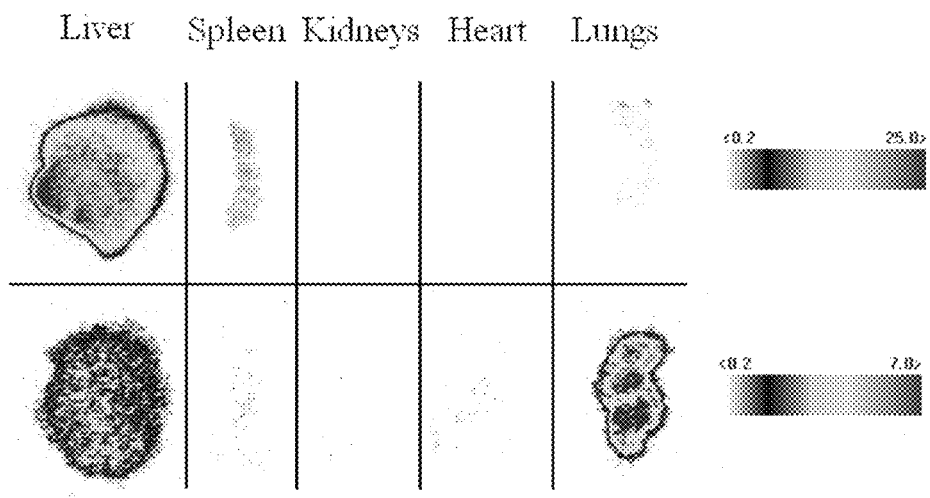

FIG. 10: Ex vivo biodistribution 15 hours after systemic injection of amino nanoparticles (top row) and RAW cells (murine macrophages) tagged with persistent luminescence nanoparticles (bottom row). These images were recorded after excitation of dissected organs in the visible range for 2 minutes. The majority locating of cells in the lungs can be seen confirming the in vivo biodistribution in FIG. 9.

Figure 11:
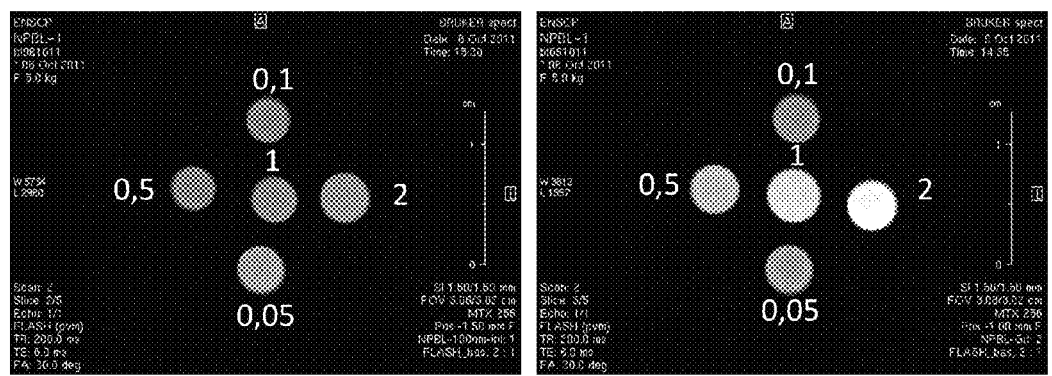

FIG. 11: MRI image obtained under T1 contrast for different concentrations (mg/mL) of nanoparticles of $ZnGa_{1.995}Cr_{0.005}O_4$ (left) and $ZnGa_{1.955}Cr_{0.005}Gd_{0.04}O_4$ (right).

Figure 12:
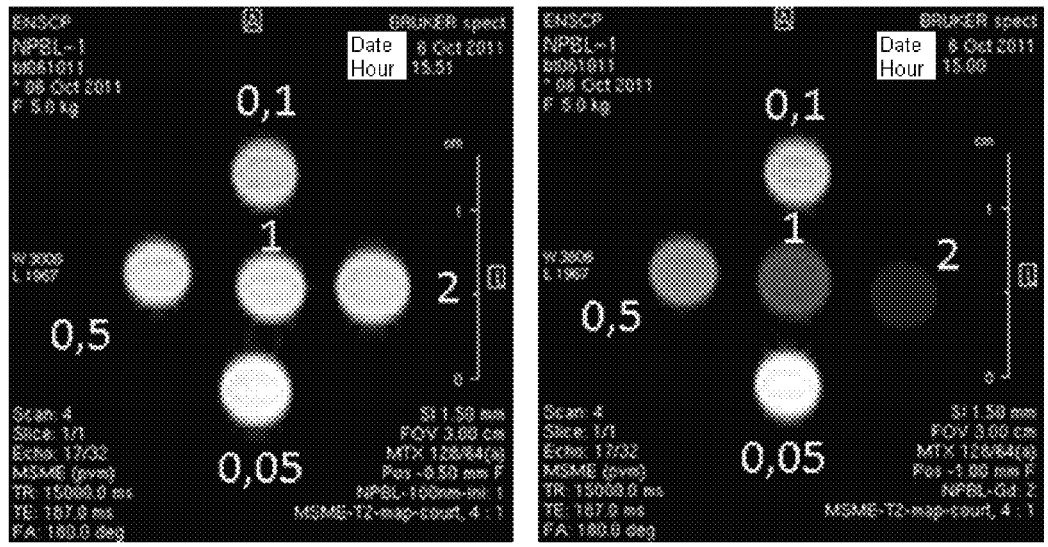

FIG. 12: MRI image obtained under T2 contrast for different concentrations (mg/mL) of nanoparticles of $ZnGa_{1.995}Cr_{0.005}O_4$ (left) and $ZnGa_{1.955}Cr_{0.005}Gd_{0.04}O_4$ (right).

Figure 13:
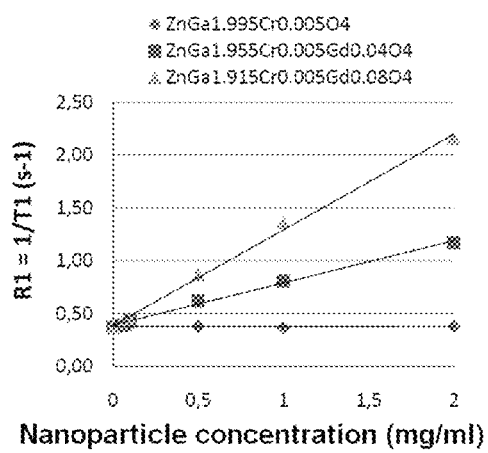
Figure 13:
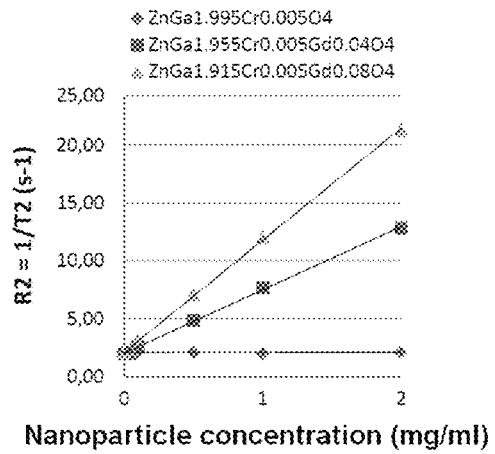

FIG. 13: Relaxivities obtained from MRI images under T1 and T2 contrast for nanoparticles of $ZnGa_{2(1-x-y)}Cr_{2x}Gd_{2y}O_4$.

Figure 14:
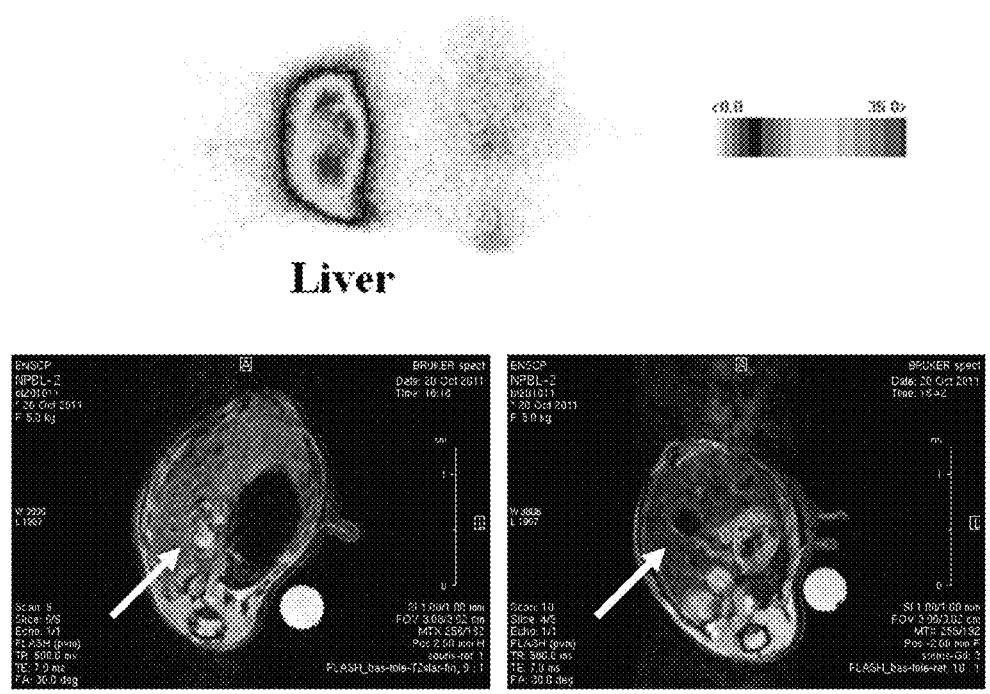

FIG. 14: Top picture: Monitoring by optical imaging of the biodistribution of non-functionalised nanoparticles doped with gadolinium, 2 mg of $ZnGa_{1.955}Cr_{0.005}Gd_{0.04}O_4$, 24 h after injection. Signal acquisition was obtained during 5-minute period after mouse exposure time of 2 minutes to a halogen source emitting at between 550 and 700 nm. Bottom picture: MRI slice (7T) of the liver of a control mouse without particles (red arrow, left picture) and of a mouse injected with the compound doped with gadolinium (red arrow, right picture). The MRI images were obtained by T2* weighting. Homogeneous negative contrast can be seen at the bulk of the liver (dark region in the right-hand picture compared with the particle-free control liver on the left).

Figure 15:
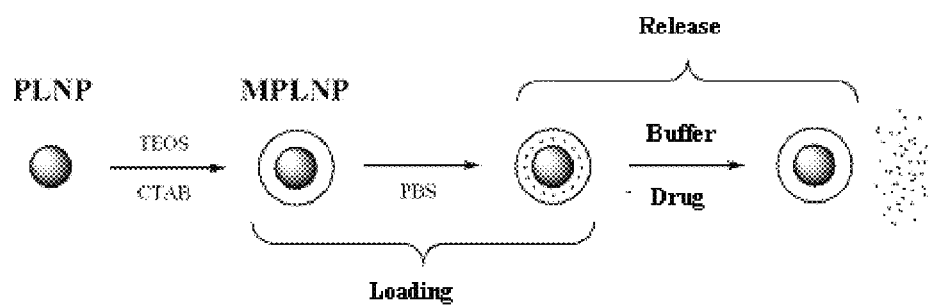

FIG. 15: Principle of the use of a mesoporous persistent luminescence structure. PLNP: <<persistent luminescence nanoparticles>>; MPLNP: <<mesoporous persistent luminescence nanoparticles>>.

Figure 16:
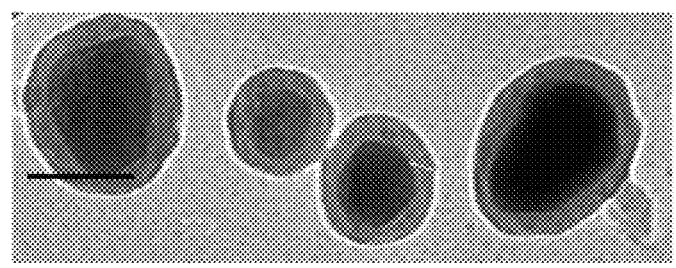

FIG. 16: Electron microscope image of $ZnGa_{1.995}Cr_{0.005}O_4$ (dark region) after formation of the mesoporous layer (light region). The bold line represents 100 nm.

Figure 17A:
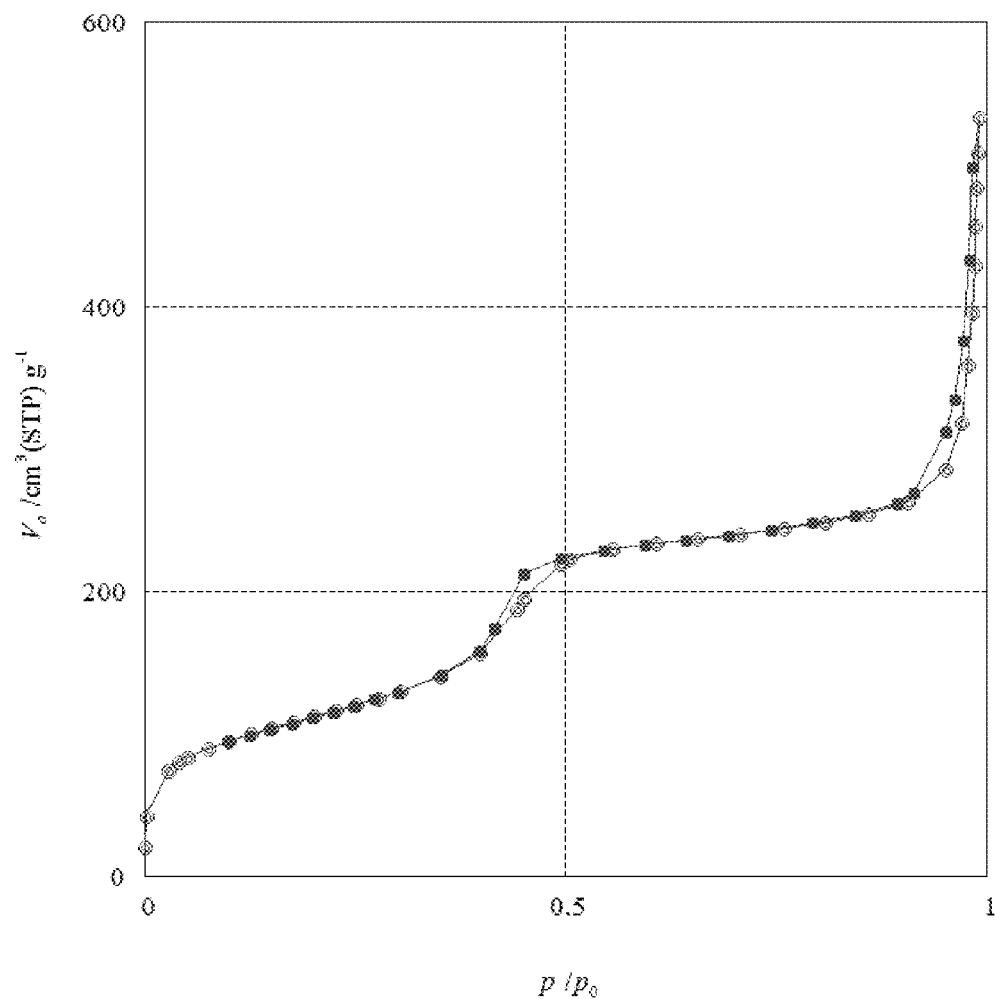
Figure 17B:
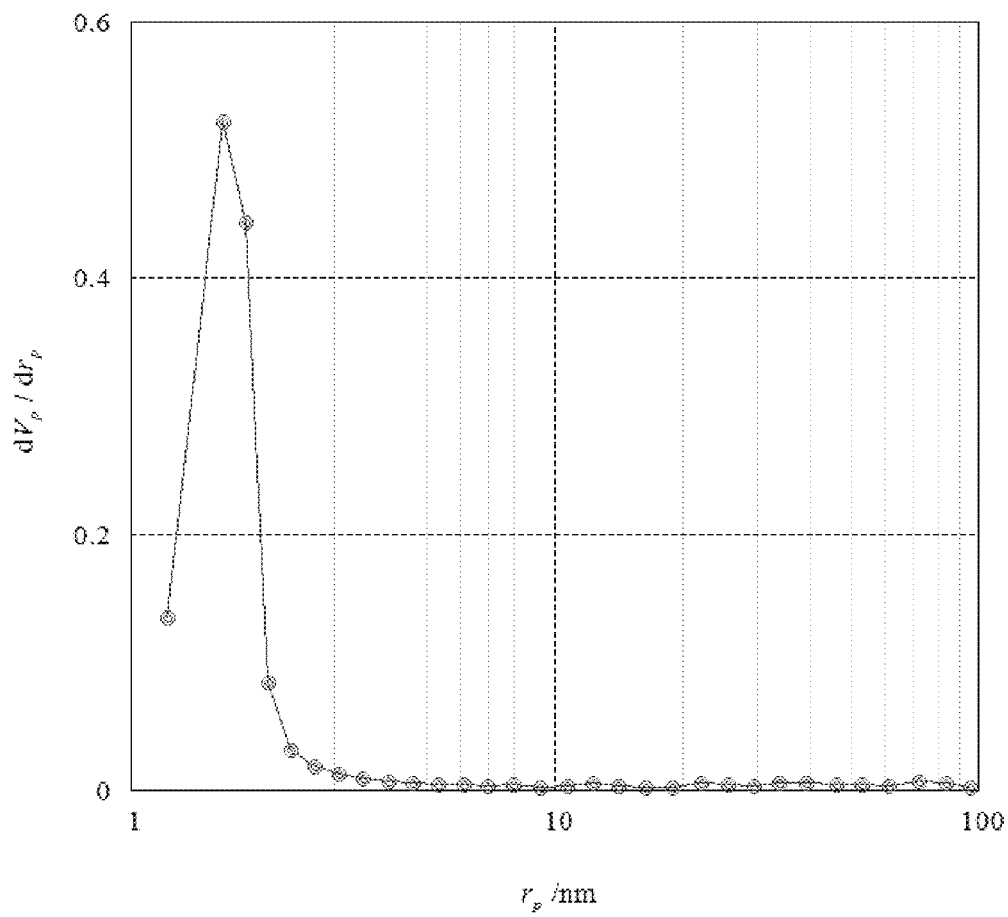
Figure 17C:
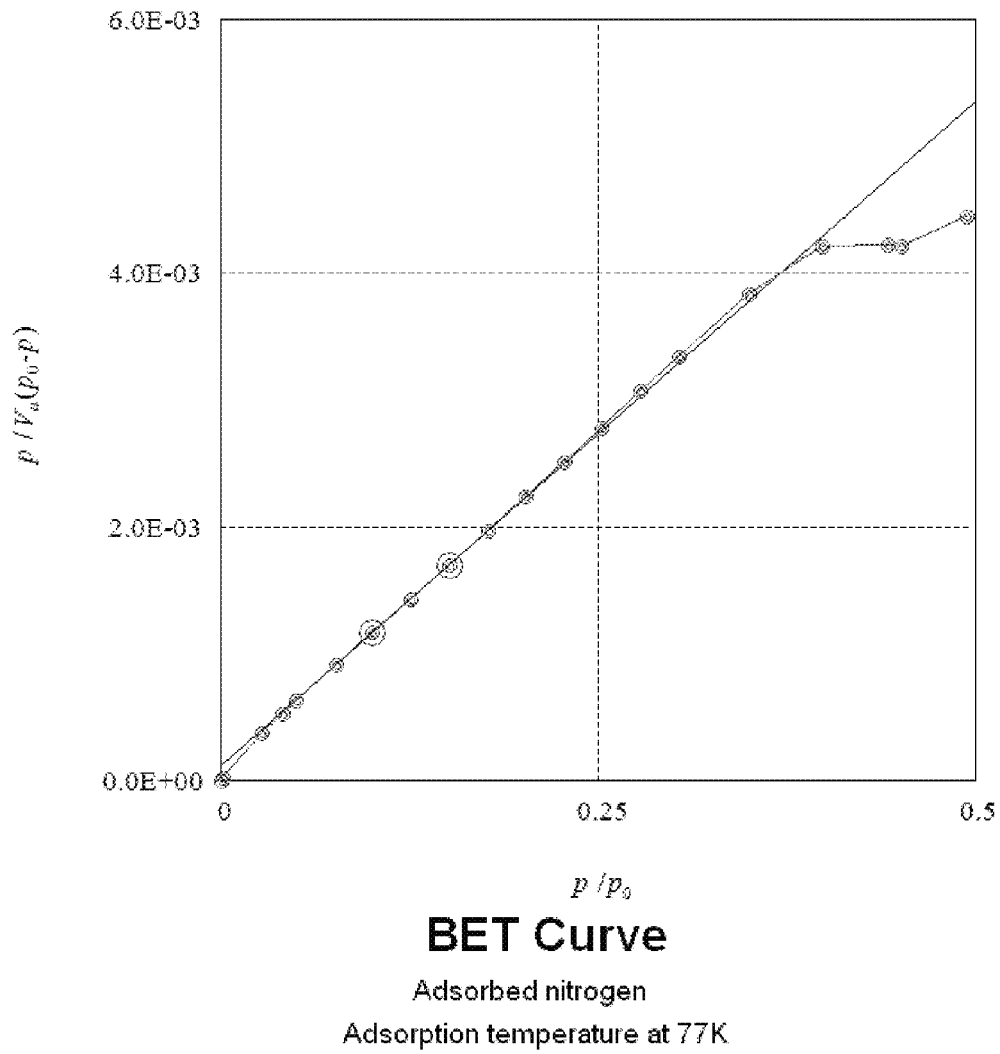

FIG. 17: Porosity parameters of mesoporous persistent luminescence nanoparticles (mean diameter about 100 nm).

Figure 18:
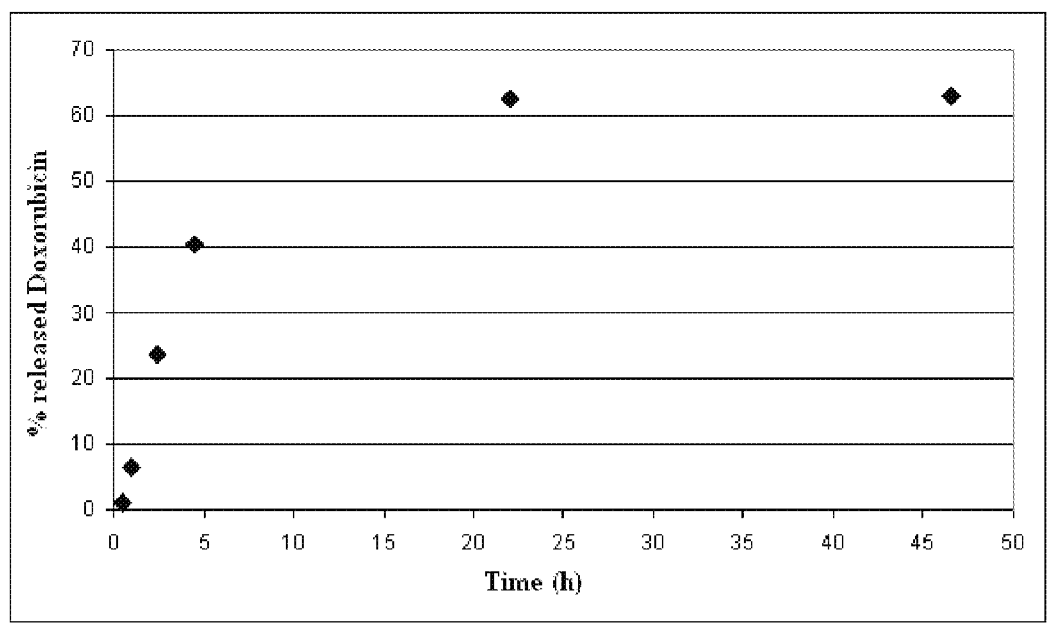

FIG. 18: Release kinetics of doxorubicin after loading DOX in mesoporous persistent luminescence nanoparticles.

Figure 19:
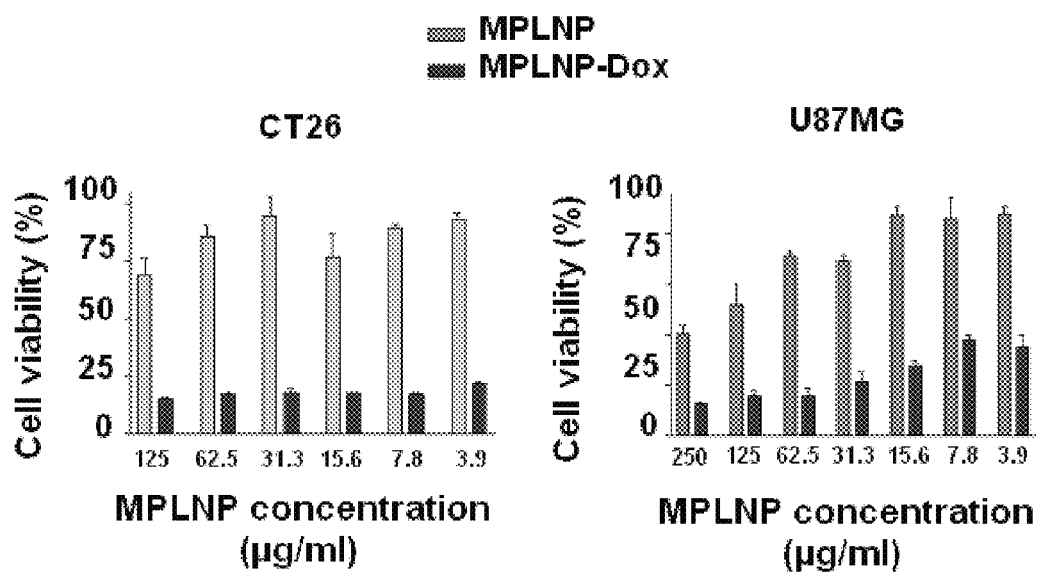

FIG. 19: MTT test after 24 h contact between mesoporous particles without doxorubicin (MPLNP), or loaded with doxorubicin (MPLNP-Dox), and two cancer cell lines. U87MG: human glioblastoma line; CT26: murine colon carcinoma line.

Figure 20:
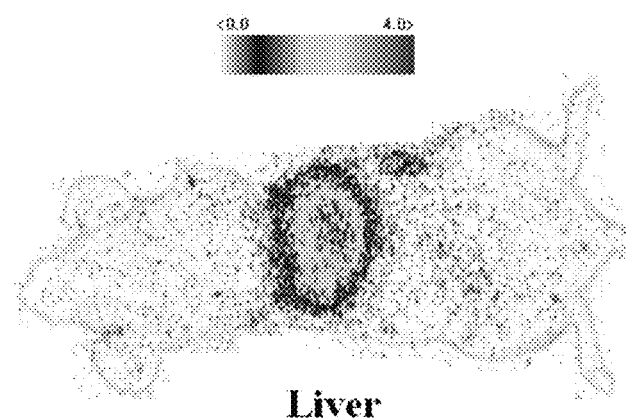

FIG. 20: Optical imaging monitoring of the biodistribution of non-functionalised mesoporous nanoparticles, 24 h after injection of 2 mg of MPLNP. Signal acquisition was obtained for 5 minutes after mouse exposure time of 2 minutes to a LED source (see FIG. 2.A for the emission spectrum).

EXAMPLES

1—Synthesis of $ZnGa_{2(1-x-y)}Cr_{2x}Gd_{2y}O_4$ with $x \in [0.001; 0.0075]$; $y \in [0.01; 0.08]$ The nanoparticles were prepared by hydrothermal synthesis. A mixture of gallium, chromium, zinc and gadolinium nitrates in desired proportions, adapted for the desired composition were dissolved in water under agitation and at ambient temperature. The addition of concentrated ammonia to this solution of cations, up to a value of pH=7.5 allowed the precipitation of a precursor of zinc gallate. The suspension was left under agitation at ambient temperature for 3 hours then transferred to a Teflon reactor to undergo treatment under pressure at 120° C. for 24 hours. The compound obtained after treatment was washed several times in water and ethanol and dried in vacuo. Finally the dried compound was ground to a fine powder and calcined at 750° C. for 5 hours.

The structure of the crystal was confirmed by X-ray diffraction. It can be seen in FIG. 1 that the compound without gadolinium, $ZnGa_{1.995}Cr_{0.005}O_4$, and the compound with gadolinium, $ZnGa_{1.955}Cr_{0.005}Gd_{0.04}O_4$, have the structure of zinc gallate: $ZnGa_2O_4$. It is also observed that the addition of these two cations ($Cr^{3+}$ and $Gd^{3+}$) does not cause the formation of any parasitic phase.

The optical properties of the nanoparticles obtained are shown in FIG. 2. It can be seen that excitation focused on 605 nm (FIG. 2.A) allows activation of the persistent luminescence signal, that is weaker but characterized by an emission spectrum centred around 700 nm (FIG. 2.C) and decay kinetics (FIG. 2.D) similar to those obtained after UV excitation. The excitation spectrum of photoluminescence at 705 nm of the compound $ZnGa_{1.995}Cr_{0.005}O_4$ can be seen (FIG. 2.B).

The addition of gadolinium leads to a drop in persistent luminescence but allows the maintaining of the same type of decay and comparable kinetics (FIG. 3).

2—Extraction of a Monodisperse Suspension of Nanoparticles of $ZnGa_{2(1-x-y)}Cr_{2x}Gd_{2y}O_4$ The nanoparticles obtained were crushed for about ten minutes then taken up in a sodium hydroxide solution (5 mM) to allow surface hydroxylation. The suspension was passed through an ultrasound bath then left under agitation overnight. Finally the nanoparticles were extracted by selective centrifugations. Precise adjustment of the centrifugation parameters allows selection of the diameter of interest. An example of nanoparticles having a diameter of 80 nm is given in FIG. 4.

3—Functionalization of Nanoparticles of $ZnGa_{2(1-x-y)}Cr_{2x}Gd_{2y}O_4$

After extraction of a monodisperse suspension, it is important to be able to modify the surface condition of the nanoparticles to promote their circulation within the body or to allow optional targeting by adding ligands of biological receptors. This functionalization is possible via successive chemical modifications on the surface of the persistent luminescence nanoparticles (FIG. 5) and allows controlling of the biodistribution of the probes after injection.

Several characterization steps ensure that functionalization has effectively taken place. Measurement of potential allows evaluation of the surface charge of these persistent luminescence nanoparticles. In particular, the adding of polyethylene glycol (PEG) allows masking of surface charges and increases the circulation time of the nanoparticles after systemic injection into a small animal.

Details and Protocols of the Functionalization Steps

Functionalization of the Nanoparticles with 3-Aminopropyltriethoxysilane (APTES):

The hydroxylated nanoparticles in suspension in dimethylformamide (DMF) at a concentration of 2.5 mg/mL were dispersed in an ultrasound bath for 5 minutes. The APTES was added thereto at a volume concentration of 5%. The suspension was again left in the ultrasound bath for 5 minutes, then left under strong agitation for 5 h. The nanoparticles were finally washed several times in ethanol to remove excess APTES.

Functionalization of the Nanoparticles with Polyethylene Glycol (PEG):

The amino nanoparticles were dissolved in DMF at a concentration of 2.5 mg/mL then dispersed in an ultrasound bath for 5 minutes. A solution of PEG 5 kDa (alpha-methoxy gamma-N-hydroxysuccinimide, 25 mg) was added to the suspension of nanoparticles. The mixture was again dispersed in an ultrasound bath 5 minutes, then left under strong agitation at 90° C. overnight. The nanoparticles were finally washed several times in DMF to remove excess APTES.

4—Injection of the Nanoparticles of $ZnGa_{1.995}Cr_{0.005}O_4$ Whether or not Functionalized, and Application of the Stealth Nanoparticles to Target CT26 Tumours It can be seen in FIG. 6 (top pictures) that there is a distinct difference in biodistribution between the negative nanoparticles and those whose charge is masked by PEG. This effect is characteristic of numerous types of nanoparticles. The negative nanoparticles, on account of their surface charge, undergo rapid opsonisation followed by capture by the liver macrophages (Kupffer cells), which can be seen in the picture on the left (FIG. 6, top picture). On the other hand, this recognition process is delayed when the surface charges are masked by adding PEG. This can be seen in the top right picture in FIG. 6. The particles are distributed more homogeneously within the body and are distributed in the general circulation.

The intravenous injection of these PEGylated nanoparticles, called stealth nanoparticles, in a mouse carrying subcutaneous CT26 tumours (FIG. 6, bottom left) allows passive targeting of the tumour region by gradual accumulation of the probe at the diseased tissues. The persistent luminescence signal then allows clear viewing of the tumours implanted in the animal (FIG. 6, bottom right).

5—Excitation of the Persistent Luminescence of the Nanoparticles Through an Animal Body One of the major weak points in the preceding generation of persistent luminescence nanoparticles lies in their incapability of being excited through animal tissue, thereby limiting observation to a time not exceeding one hour. The acquisitions of persistent luminescence signals presented below indicate that these compounds ($ZnGa_{2(1-x-y)}Cr_{2x}Gd_{2y}O_4$), in the form of nanoparticles can be excited through animal tissue to obtain a persistent luminescence signal. With this innovation it is possible to avoid any time constraint and to observe the nanoparticles at any time.

For this procedure the mice were anesthetised with a ketamine/xylazine mixture and injected with the nanoparticles of $ZnGa_{1.995}Cr_{0.005}O_4$ in the tail vein. The mice were placed under the LED system (see FIG. 2.A for the emission spectrum) for 2 minutes to excite persistent luminescence, then placed under an ICCD camera (photon count system, Biospace Lab). It can be seen in FIG. 7 that the persistent luminescence signal allows the locating of the particles and monitoring of their biodistribution after several hours.

6—Example of Application to Real-Time Cell Monitoring in Mice

As an original example of the application of this technology, we also report on the possibility of marking the cells with these persistent luminescence nanoparticles, and of tracking their cell biodistribution after systemic injection into a small animal:

Marking of RAW Cells (Murine Macrophages) and Injection:

Marking of cells was obtained by incubating RAW macrophages ($10^6$ per well, 6-well plate), with 2 mL of a suspension of nanoparticles in DMEM serum-free culture medium (1 mg/mL) for 6 h. After incubation, the cells were washed several times in the culture medium to remove excess nanoparticles, taken up in the same medium and concentrated by centrifugation at 900 rpm for mouse injection (300 μL). Efficient marking of the cells can be verified by exciting persistent luminescence with the LED system (FIG. 8).

In vivo study was performed by comparing the biodistribution of amino nanoparticles, 2 mg in suspension in the serum-free culture medium, injected into the tail vein, with the biodistribution of the macrophages tagged with the nanoparticles ($10^6$ cells) in suspension in the same medium. The results are given in FIG. 9.

A distinct difference in biodistribution is seen between the particles alone and the tagged macrophages. The particles alone are concentrated at the liver for the same reasons as those given above. The tagged cells are attached to the lungs.

Re-excitation through the tissues also allows ex vivo quantification after organ sampling (the excitation conditions are the same as previously with the LED system). The luminescence images obtained are given in FIG. 10.

7—Example of Application of $ZnGa_{2(1-x-y)}Cr_{2x}Gd_{2y}O_4$ for Multimodal Imaging It has already been pointed out above that the adding of gadolinium to the zinc gallate structure does not alter the nature of the optical properties. In particular, the phenomenon of persistent luminescence, less intense it is true, is maintained as are the excitability properties of the material above 600 nm (LED system, FIG. 2.A).

The nanoparticles used for measuring relaxation times (T1 and T2) in vitro were prepared following the protocol described in the two first parts. The nanoparticles have a diameter of about 80 nm.

It can be seen in FIGS. 11 and 12 (left pictures) that the nanoparticles non-doped with gadolinium do not display any concentration-dependent contrast effect (same contrast at the circles) and show relaxivity values similar to those of the control (without nanoparticles). On the other hand, the relaxivity measurements R1 and R2, and the images obtained with 7T MRI (FIGS. 11, 12, on the right; then FIG. 13), indicate a T1 and T2 effect of the nanoparticles related to the addition of gadolinium. This effect is indeed dependent on nanoparticle concentration: the greater the concentration the greater the contrast. Comparisons with T1 and T2 relaxivity values of commercial agents (Dotarem and Endorem), in the light of the relaxivities calculated for the nanoparticles of $ZnGa_{2(1-x-y)}Cr_{2x}Gd_{2y}O_4$, place us in a position to say that the T2 effect is preponderant (supported by calculation of the ratio R2/R1>1).

Example of In Vivo Application to Small Animals:

At an initial step, optical imaging allowed locating of the particles after intravenous injection. The accumulation of persistent luminescence nanoparticles at the liver was monitored by optical imaging 24 hours after injection (FIG. 14, 2 mg of $ZnGa_{1.955}Cr_{0.005}Gd_{0.04}O_4$ diameter of 80 nm, in suspension in 5% glucose for injection). MRI acquisition with T2 contrast allowed confirmed presence of the nanoparticles distributed homogeneously in the bulk of the liver (as compared with the control liver not having received any particle). This type of diffuse negative contrast at the liver is characteristic of capture by the organ's macrophages, Kupffer cells.

8—Synthesis of Mesoporous Persistent Luminescence Nanoparticles (MPLNP)

The principle underlying the use of mesoporous persistent luminescence nanoparticles for theranostic applications is summarised in FIG. 15.

Example of Synthesis with $ZnGa_{1.99}Cr_{0.005}O_4$:

The mesoporous layer was formed by condensation of tetraethoxysilane (TEOS) around the nanoparticles in the presence of a cationic surfactant: cetyltrimethylammonium bromide (CTAB).

The nanoparticles were suspended in a CTAB solution (4 mg/mL) in 5 mM sodium hydroxide at a concentration of 1 mg/mL. The mixture was well dispersed in an ultrasound bath and left at 45° C. under strong agitation. TEOS was then added dropwise to the suspension of nanoparticles to obtain a final concentration of 1% by volume (ex.: 10 μL of TEOS per 1 mL of suspension). After an agitation time of 3 hours at 45° C., the suspension was transferred to a Teflon reactor to undergo maturing under pressure for 24 h at 100° C. The suspension was finally washed several times in water and ethanol to remove excess surfactant.

The porous structure was obtained by extraction of the surfactant (CTAB) from the silica layer coating the persistent luminescence nanoparticles. This extraction was performed in a solution of NaCl in methanol (1% by weight). The nanoparticles are suspended in this saline solution of methanol and left under agitation for 3 h. After extraction, the nanoparticles were washed several times in ethanol. This extraction step was repeated 3 times to ensure that all the surfactant had effectively been removed.

FIG. 16 gives an electron microscope image of the core-shell structure obtained after encapsulation of the gallate crystals in a layer of mesoporous silica. The crystal at the core of the structure can clearly be seen being of greater density since less transparent to the electrons, and the layer of amorphous silica that is light-coloured in the image on account of its transparency to electrons. The porosity parameters were determined by nitrogen adsorption at 77 K.

The results in FIG. 17 indicate an accessible specific surface area of 400 $m^2/g$ of compound. The pore diameter is about 2 nm.

9—Example of Application of MPLNPs to Deliver Cytotoxic Molecules

The idea was to use this structure to administer active ingredients and we therefore conducted a first proof of concept study with doxorubicin (Dox), used in the clinical treatment of some cancers. This molecule distinctly absorbs light at around 480 nm. For this reason the loading of Dox into the porous structure was followed by measurement of absorbance at 480 nm. We evaluated the amount of Dox (unit weight of particles) at 150 μg per mg of mesoporous nanoparticles. The same assay technique was used to evaluate the release kinetics of the compound in a phosphate buffer (FIG. 18).

With a view to evaluating the possibility of using these nanoparticles to convey and release a cytotoxic molecule we compared the toxicity of the nanoparticles loaded with Dox (MPLNP-Dox) with that of non-loaded nanoparticles (MPLNP) on several cell lines (CT26 and U87MG).

Assay protocol: The cells were cultured and placed in 96-well plates at a concentration of 10000 cells/well. The toxicity assay (MTT) was performed 24 hours after depositing the nanoparticles at different concentrations on the cells. The results are given in FIG. 19. The clearly-defined toxicity can be seen of the nanoparticles loaded with doxorubicin compared with the control nanoparticles (non-loaded).

Finally, we demonstrated in vivo that the formation of the mesoporous silica layer on these persistent luminescence nanoparticles does not prevent excitation of persistent luminescence through the tissues. The picture in FIG. 20 shows the persistent luminescence signal obtained after excitation in the visible range (LED system, see FIG. 2.A) in a mouse injected with the MPLNPs.

REFERENCES

Patent References

WO 2007/048856
FR 2 908 891

Non-Patent References le Masne de Chermont, Quentin, Corinne Chandac, Johanne Seguin, Fabienne Pellé, Serge Maîrejean, Jean-Pierre Jolivet, Didier Gourier, Michel Bessodes, and Daniel Scherman. "Nanoprobes with near-infrared persistent luminescence for in vivo imaging." Proceedings of the National Academy of Sciences of the United States of America 104, no. 22 (May 29, 2007): 9266-71.

Pan, Zhengwei, Yi-Ying Lu, and Feng Liu. "Sunlight-activated long-persistent luminescence in the near-infrared from Cr3+-doped zinc gallogermanates." Nature Materials 11, no. 1 (Nov. 20, 2011): 58-63. http://www.nature.com/doifinder/10.1038/nmat3173.

Bessière, Aurélie, Sylvaine Jacquart, Kaustubh Priolkar, Aurélie Lecointre, Bruno Viana, and Didier Gourier. "ZnGa2 O4:Cr 3+: a new red long-lasting phosphor with high brightness." Optics Express 19, no. 11 (2011): 10131-10137.

Liu, Yanlan, Kelong Ai, Qinghai Yuan, and Lehui Lu. "Fluorescence-enhanced gadolinium-doped zinc oxide quantum dots for magnetic resonance and fluorescence imaging." Biomaterials 32, no. 4 (February 2011): 1185-92. http://www.ncbi.nlm.nih.gov/pubmed/21055806.

Kim, Jaeyun, Hoe Suk Kim, Nohyun Lee, Taeho Kim, Hyoungsu Kim, Taekyung Yu, In Chan Song, Woo Kyung Moon, and Taeghwan Hyeon. "Multifunctional Uniform Nanoparticles Composed of a Magnetite Nanocrystal Core and a Mesoporous Silica Shell for Magnetic Resonance and Fluorescence Imaging and for Drug Delivery." Angewandte Chemie 120, no. 44 (Oct. 20, 2008): 8566-8569. http://doi.wiley.com/10.1002/ange.200802469.

Kang, Xiaojiao, Ziyong Cheng, Chunxia Li, Dongmei Yang, Mengmeng Shang, Ping Ma, Guogang Li, Nian Liu, and Jun Lin. "Core-Shell Structured Up-Conversion Luminescent and as Carriers for Drug Delivery" (2011).

Xu, Zhenhe, Yu Gao, Shanshan Huang, Ping'an Ma, Jun Un, and Jiye Fang. "A luminescent and mesoporous core-shell structured Gd2O3: Eu(3+)@nSiO2@mSiO2 nanocomposite as a drug carrier." Dalton transactions (Cambridge, England: 2003) 40, no. 18 (May 14, 2011): 4846-54. http://www.ncbi.nlm.nih.gov/pubmed/21431226.

J. S. Kim, J. S. Kim, H. L. Park, Solid State Communications 131 (2004) 735-738.

The invention claimed is:

1. An in vivo optical imaging method of a human or animal body, comprising the following steps:
    a) exciting the persistent luminescence of nanoparticles by in vivo irradiation of all or part of the human or animal body at a wavelength between 550 and 1000 nm, said nanoparticles being previously administered to the human or animal body, and said nanoparticles emitting photons at wavelengths between 550 and 1000 nm for at least 0.01 second, after light excitation at wavelengths between 550 and 1000 nm, and said nanoparticles comprising a nanomaterial formed of a matrix selected from among gallates, aluminates, indates, and their mixed compounds gallo-germanates, gallo-aluminates, gallo-indates, gallium oxides, indium oxides, magnesium oxides, zinc and gallium oxysulfides, zinc and gallium oxyselenides, zinc and gallium oxytellurides, said matrix being doped with a transition metal or lanthanide selected from among chromium, europium, cerium, nickel, iron, copper and cobalt; and
    b) detecting the nanoparticles in vivo in all or part of the human or animal body by measuring the persistent luminescence of the nanoparticles via optical imaging.

2. The in vivo optical imaging method of a human or animal body according to claim 1, wherein said nanoparticles comprise the nanomaterial $ZnGa_{2(1-x)}Cr_{2x}O_4$ with x between 0.001 and 0.0075.

3. The in vivo optical imaging method of a human or animal body according to claim 1, wherein said nanoparticles comprise the nanomaterial $ZnGa_{1.995}Cr_{0.005}O_4$.

4. The in vivo optical imaging method of a human or animal body according to claim 1, wherein the administering of the nanoparticles is previously performed via intravenous, intra-arterial, intramuscular, intraperitoneal or retro-orbital route.

5. The in vivo optical imaging method of a human or animal body according to claim 1, wherein the size of the nanoparticles is between 1 and $10^3$ nm.

6. The in vivo optical imaging method of a human or animal body according to claim 1, wherein the nanoparticles are surface grafted or coated.

7. The in vivo optical imaging method of a human or animal body according to claim 1, wherein the nanoparticles are surface grafted with a ligand.

8. The in vivo optical imaging method of a human or animal body according to claim 1, wherein the nanoparticles are encapsulated in mesoporous silica allowing the loading and release of molecules of interest.

9. A bimodal in vivo imaging method of a human or animal body comprising the following steps:
    a) exciting the persistent luminescence of the nanoparticles by in vivo irradiation of all or part of the human or animal body at a wavelength between 550 and 1000 nm, said nanoparticles being previously administered to the human or animal body, and said nanoparticles emitting photons at wavelengths between 550-1000 nm for at least 0.01 second under excitation light at wavelengths between 550 and 1000 nm, said nanoparticles having paramagnetic properties and said nanoparticles comprising a nanomaterial formed of a matrix from among gallates, aluminates, indates, gallium oxides, indium oxides, magnesium oxides, gallo-germanates, alumina-gallates, zinc and gallium oxysulfides, zinc an gallium oxyselenides, zinc and gallium oxytellurides, said matrix being doped with a transition metal or lanthanide selected from among chromium, europium, cerium, nickel, iron, copper and cobalt and with at least one paramagnetic element selected from among $Cr^{3+}$; $Mn^{2+}$; $Gd^{3+}$; $Fe^{3+}$ and $Ni^{3+}$;

b) detecting the nanoparticles in vivo in all or part of the human or animal body by measuring the persistent luminescence of the nanoparticles using optical imaging; and c) detecting the nanoparticles in vivo in all or part of the human or animal body by magnetic resonance imaging.

10. The in vivo bimodal imaging method of a human or animal body according to claim 9 wherein said nanoparticles comprise the nanomaterial $ZnGa_{2(1-x-y)}Cr_{2x}Gd_{2y}O_4$ with x between 0.001 and 0.0075 and y between 0.01 and 0.08.

11. The in vivo bimodal imaging method of a human or animal body according to claim 9, wherein said nanoparticles comprise the nanomaterial $ZnGa_{1.955}Cr_{0.005}Gd_{0.04}O_4$.

12. The in vivo bimodal imaging method of a human or animal body according to claim 9, wherein the administering of the nanoparticles is previously performed via intravenous, intra-arterial, intramuscular, intraperitoneal or retro-orbital route.

13. The in vivo bimodal imaging method of a human or animal body according to claim 9, wherein the size of the nanoparticles is between 1 and $10^3$ nm.

14. The in vivo bimodal imaging method of a human or animal body according to claim 9, wherein the nanoparticles are surface grafted or coated.

15. The in vivo bimodal imaging method of a human or animal body according to claim 9, wherein the nanoparticles are grafted with a ligand.

16. The in vivo bimodal imaging method of a human or animal body according to claim 9, wherein the nanoparticles are encapsulated in mesoporous silica allowing the loading and release of molecules of interest.

17. A nanoparticle comprising the nanomaterial $ZnGa_{2(1-x-y)}Cr_{2x}Gd_{2y}O_4$ with x between 0.001 and 0.0075 and y between 0.01 and 0.08.

18. The nanoparticle according to claim 17 characterized in that the nanomaterial is $ZnGa_{1.955}Cr_{0.005}Gd_{0.04}O_4$.

19. The nanoparticle according to claim 17, characterized in that its size is between 1 and $10^3$ nm.

* * * * *